(12) United States Patent
Salpeter

(10) Patent No.: US 12,350,490 B2
(45) Date of Patent: Jul. 8, 2025

(54) ELECTROTHERAPY GLOVE FOR DELIVERY OF AMPLITUDE MODULATED PULSED DIRECT CURRENT DURING MANUAL THERAPY TREATMENT

(71) Applicant: Neurological Fitness Equipment and Education LLC, Austin, TX (US)

(72) Inventor: Garrett Salpeter, Austin, TX (US)

(73) Assignee: Neurological Fitness Equipment and Education LLC, Austin, TX (US)

( * ) Notice: Subject to any disclaimer, the term of this patent is extended or adjusted under 35 U.S.C. 154(b) by 437 days.

(21) Appl. No.: 17/736,516

(22) Filed: May 4, 2022

(65) Prior Publication Data
US 2023/0355970 A1    Nov. 9, 2023

(51) Int. Cl.
*A61N 1/36* (2006.01)
*A41D 19/00* (2006.01)
(Continued)

(52) U.S. Cl.
CPC ..... *A61N 1/36014* (2013.01); *A41D 19/0024* (2013.01); *A61H 99/00* (2013.01);
(Continued)

(58) Field of Classification Search
CPC .............. A61N 1/36014; A61N 1/0472; A41D 19/0024; A41D 2400/322; A61H 99/00; A61H 2201/10
(Continued)

(56) References Cited

U.S. PATENT DOCUMENTS

| | | |
|---|---|---|
| 5,070,862 A | 12/1991 | Berlant |
| 5,107,835 A | 4/1992 | Thomas |

(Continued)

FOREIGN PATENT DOCUMENTS

| | | | |
|---|---|---|---|
| JP | H07194711 A | * 8/1995 | |
| WO | WO-2019078365 A1 | * 4/2019 | ............. A61H 39/00 |

OTHER PUBLICATIONS

P.M. Biesheuvel et al., "The Difference between Faradaic and non-Faradaic electrode processes," 16 pages, Jan. 11, 2021.
(Continued)

*Primary Examiner* — Michael J Lau
(74) *Attorney, Agent, or Firm* — Prol Intellectual Property Law, PLLC; H. Kenneth Prol

(57) ABSTRACT

An amplitude-modulated pulsed direct current (DC) electrotherapy system may comprise an electrotherapy glove for insertion of a practitioner's hand and an exterior surface including an electrically conductive patient-contact surface for contacting a patient's skin during an electrotherapy-assisted physical manipulation treatment of the patient's muscle within a physical manipulation target region, a signal generator operably connected to the glove via an electrically conductive interface to deliver an amplitude-modulated pulsed DC electrical signal to the target region via the patient-contact regions of the glove, the amplitude-modulated pulsed DC electrical signal having an alternating current electrical signal for inhibiting painful sensation in the patient's skin within the target region due to application of the amplitude-modulated pulsed DC electrical signal mixed with a pulsed DC electrical signal frequency and amplitude capable of inducing relaxation of the patient's muscle to increase a portion thereof accessible to the practitioner for physical manipulation during the electrotherapy-assisted physical manipulation treatment.

20 Claims, 12 Drawing Sheets

(51) Int. Cl.
*A61H 99/00* (2006.01)
*A61N 1/04* (2006.01)

(52) U.S. Cl.
CPC ...... *A61N 1/0472* (2013.01); *A41D 2400/322* (2013.01); *A61H 2201/10* (2013.01)

(58) Field of Classification Search
USPC .......................................................... 607/3
See application file for complete search history.

(56) References Cited

U.S. PATENT DOCUMENTS

| | | | | |
|---|---|---|---|---|
| 5,374,283 | A | * | 12/1994 | Flick ....................... A61N 1/321 |
| | | | | 607/152 |
| 5,674,261 | A | | 10/1997 | Smith |
| 7,725,193 | B1 | | 5/2010 | Chu |
| 9,757,302 | B2 | | 9/2017 | Mayer |
| 10,639,476 | B2 | | 5/2020 | Chang |
| 11,027,123 | B2 | | 6/2021 | Boggs |
| 11,179,563 | B2 | | 11/2021 | O |
| 2007/0179534 | A1 | * | 8/2007 | Firlik ................ A61M 5/14276 |
| | | | | 604/503 |
| 2010/0318009 | A1 | * | 12/2010 | Stanley ................ A61N 1/0484 |
| | | | | 602/5 |
| 2010/0324626 | A1 | | 12/2010 | Lefkovitz |
| 2011/0022115 | A1 | * | 1/2011 | Salzhauer ............ A61N 1/0456 |
| | | | | 607/46 |
| 2013/0282070 | A1 | * | 10/2013 | Cowan ............... A61N 1/36071 |
| | | | | 607/45 |
| 2015/0083704 | A1 | * | 3/2015 | Guidry ............. A41D 19/01535 |
| | | | | 219/211 |
| 2016/0346529 | A1 | * | 12/2016 | Cazares Delgadillo ..................... |
| | | | | A61N 1/327 |
| 2016/0346540 | A1 | * | 12/2016 | Wijting ............... A61N 1/36034 |
| 2017/0224990 | A1 | * | 8/2017 | Goldwasser .......... A61N 1/0476 |
| 2018/0015284 | A1 | * | 1/2018 | Coleman ................. G16H 40/63 |
| 2018/0318585 | A1 | * | 11/2018 | Pfeifer ............... A61N 1/36021 |
| 2019/0209835 | A1 | | 7/2019 | O |
| 2020/0023183 | A1 | * | 1/2020 | Ollerenshaw ...... A61N 1/36146 |
| 2020/0030606 | A1 | | 1/2020 | Boggs, II |
| 2020/0121926 | A1 | * | 4/2020 | Tinoosh ................. A61H 1/008 |
| 2020/0222686 | A1 | * | 7/2020 | Peiffer ................... A61N 1/303 |
| 2021/0023363 | A1 | | 1/2021 | O |

OTHER PUBLICATIONS

J.H. Shin, "One-directional flow of ionic solutions along fine electrodes under an alternating current electric field," 9 pages, May 23, 2018.

RS Medical, "How to Compare TENS Units—A Review of 5 Signal Types,"14 pages, Apr. 25, 2019.

* cited by examiner

ELECTROTHERAPY GLOVE FOR DELIVERY OF AMPLITUDE MODULATED PULSED DIRECT CURRENT DURING MANUAL THERAPY TREATMENT

FIELD OF THE DISCLOSURE

The present disclosure generally relates to electrotherapy techniques for releasing muscles of a patient during physical manipulation therapy. More specifically, the present disclosure relates to electrotherapy using an amplitude-modulated direct current pulse applied to the patient, via an electrically conductive electrotherapy glove worn by a practitioner, to decrease contraction or tone of patient muscles undergoing physical manipulation and enhance benefits of such physical manipulation.

BACKGROUND

Manual therapy, including massage, is a proven treatment method for management and reduction of chronic pain, recovery from injury or surgery, and increasing physical fitness and performance. A vital aspect of manual therapy includes encouraging circulatory movement and relaxing muscles through physical manipulation of injured, overused, or weakened muscles. However, a patient may unconsciously tense or contract those muscles, or nearby muscles in order to protect what the patient's body perceives as a vulnerable area. Such tensing, contracting, or "guarding" may make it more difficult for a manual therapist to access these vulnerable areas and to provide the therapeutic physical manipulations needed in order to encourage healing and decrease acute or chronic pain. The application of an electrical current to one or more of these muscles, via a technique called electrotherapy has been shown to reduce such guarding, allowing the manual therapy practitioner to access deeper into muscle tissue for more in-depth physical manipulation.

BRIEF DESCRIPTION OF THE DRAWINGS

It will be appreciated that for simplicity and clarity of illustration, elements illustrated in the Figures are not necessarily drawn to scale. For example, the dimensions of some elements may be exaggerated relative to other elements. Embodiments incorporating teachings of the present disclosure are shown and described with respect to the drawings herein, in which.

The use of the same reference symbols in different drawings may indicate similar or identical items.

DETAILED DESCRIPTION OF THE DRAWINGS

Figure 1:
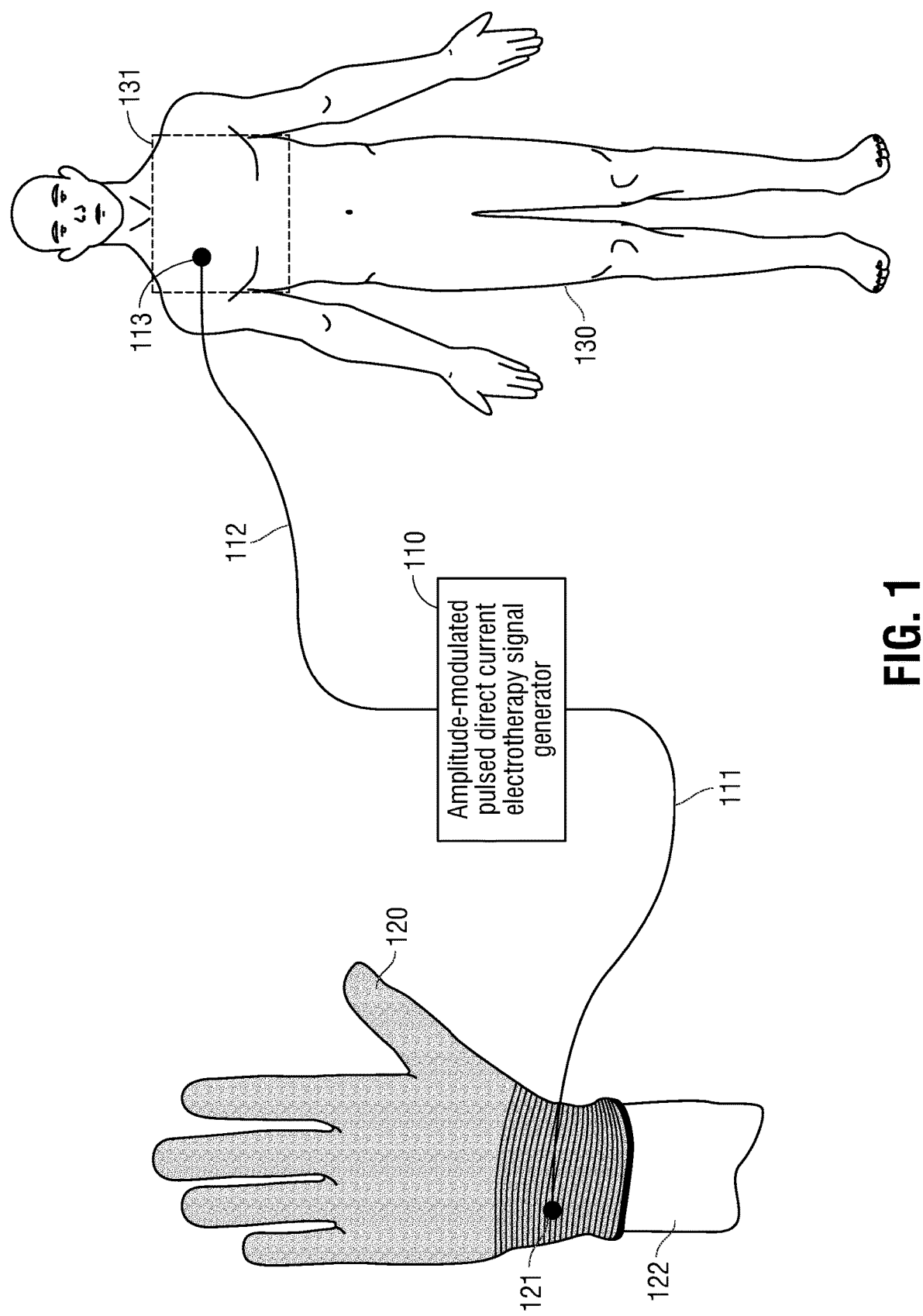
FIG. 1 is a graphical diagram illustrating application of an amplitude-modulated pulsed direct current (DC) electrical signal to an electrode on a patient and to an electrotherapy glove according to an embodiment of the present disclosure.

The following description in combination with the Figures is provided to assist in understanding the teachings disclosed herein. The description is focused on specific implementations and embodiments of the teachings, and is provided to assist in describing the teachings. This focus should not be interpreted as a limitation on the scope or applicability of the teachings.

Electrotherapy reduces unconscious muscle contraction or tensing during physical manipulation treatment, allowing a practitioner to access deeper into muscle tissue for more in-depth physical manipulation of injured, overworked, or weakened muscles. Such in-depth manipulation may promote quicker healing and more effectively decrease acute or chronic pain associated with muscular or soft tissue injury. Existing electrotherapy systems apply an electrical current to a patient's musculature or soft tissue via one or more electrodes or similar structures placed in contact with a patient's skin.

The electrical signals applied to a patient in such a way may employ alternating current (AC) or direct current (DC) of varying frequencies, amplitudes (e.g., describing voltage), or patterns. For example, many existing systems apply a pulsed DC electrical signal because DC signals pulsed at high frequencies (e.g., 100 to 1000 Hz) have been shown to decrease muscle contraction. Such muscle relaxation may enable a practitioner to access deeper into the muscle during therapeutic physical manipulation.

However, such DC signals may cause a Faradaic reaction within the patient's skin or adipose tissue situated nearby or in contact with the electrode delivering the DC signal, in which charged particles (e.g., electrons or ions) transfer across the electrode and into the patient's skin or tissue. These ions may then reduce or oxidize to another species within the patient's tissues, which may further cause a patient to experience a prickling, hot, or painful sensation at the site of application. Some existing electrotherapy systems have adapted to this obstacle by employing an AC signal, rather than a DC signal. Alternating current signals inhibit the transfer of charged particles across the electrode and into the patient's skin or adipose tissue. Thus, application of an AC signal decreases or inhibits the prickling, hot, or painful sensations felt by patients during application of direct current. However, AC signals of the same frequencies (e.g., 100 to 1000 Hz) used in application of DC signals have been shown to cause muscle contraction, rather than the muscle relaxation caused by application of DC signals.

Embodiments of the present disclosure employ an electrical signal that combines a DC signal with an AC signal to attain the benefits of each. For example, the electrical signal employed in embodiments of the present disclosure is generated with a DC electrical signal pulsed at a frequency high enough to cause muscle relaxation. An AC signal may be superimposed or mixed with this pulsed DC electrical signal in embodiments described herein in order to inhibit the transfer of charged particles across electrodes carrying the signal and applied to the patient. Thus, the combined or mixed signal that includes both a pulsed DC electrical signal and an AC signal may cause relaxation of the patient's muscles while avoiding the prickling, hot, or painful sensations caused by application of DC current alone. Mixing of the AC signal with the DC electrical signal in such a way may effectively modulate the amplitude (e.g., describing total voltage from both the underlying pulsed DC electrical signal and the AC signal) of the pulsed DC electrical signal, resulting in an amplitude-modulated pulsed DC electrical signal.

The amplitude-modulated pulsed DC electrical signal in embodiments described herein may be applied to a patient during physical manipulation of a patient's musculature or soft tissues (e.g., physical manipulation treatment) by a practitioner via an electrotherapy glove worn by the practitioner. Such an electrotherapy glove may deliver the amplitude-modulated pulsed DC electrical signal through one or more electrodes situated at various locations along the exterior surface of the electrotherapy glove, or through electrically conductive fibers interwoven within the exterior surface of the electrotherapy glove. Electrodes may be placed along the exterior of the electrotherapy glove at positions relative to the practitioner's hand commonly used in various physical manipulation techniques, as described in various embodiments of the present disclosure. Amplitudes and frequencies for the pulsed DC electrical signal of the amplitude-modulated pulsed direct current electrical signal may be optimized in various embodiments for specific types of physical manipulation methods, or treatment locations on a patient's musculature. In such a way, the amplitude-modulated pulsed direct current electrotherapy system may allow a practitioner to manipulate a patient's tissue made more accessible due to muscle relaxation resulting from application of the electrotherapy via an electrotherapy glove worn by the practitioner during such physical manipulation.

FIG. 1 is a graphical diagram illustrating application of an amplitude-modulated pulsed DC electrical signal to an electrode within a physical manipulation target region of a patient's musculature via an electrotherapy glove worn by a practitioner performing physical manipulation treatment according to an embodiment of the present disclosure. As described herein, electrotherapy reduces unconscious muscle contraction or tensing during physical manipulation treatment, allowing a practitioner to access deeper into muscle tissue for more in-depth physical manipulation of injured, overworked, or weakened muscles. Such in-depth manipulation may promote quicker healing and more effectively decrease acute or chronic pain associated with muscle or soft tissue injury.

An amplitude-modulated pulsed direct current electrotherapy signal generator 110 in an embodiment may transmit an amplitude-modulated pulsed DC electrical signal to an electrode 113 situated within a physical manipulation target region 131 of a patient's musculature via an electrically conductive cable or wire 112. In other embodiments, the electrode 113 may be placed anywhere on the patient's body in which the electrode may come into direct contact with the patient's skin. In an embodiment, the amplitude-modulated pulsed direct current electrotherapy signal generator 110 may also transmit the amplitude-modulated pulsed DC electrical signal to a receiving port 121 of an electrotherapy glove 120 worn by a practitioner 122, via an electrically conductive cable or wire 111. As described in greater detail with respect to FIG. 6, below, the amplitude-modulated pulsed DC electrical signal in an embodiment may mix a pulsed DC signal with an AC signal to attain the benefits of each.

The practitioner 122 in an embodiment may use the electrotherapy glove 120 to perform a physical manipulation of the patient's soft tissue or musculature within the physical manipulation target region 131 during delivery of the amplitude-modulated pulsed DC electrical signal to both the electrode 113 and the port 121. In another embodiment, the practitioner 122 may use the electrotherapy glove 120 to identify or diagnose the physical manipulation target region 131. For example, an electrotherapy-assisted physical manipulation session in an embodiment may begin with a patient 130 identifying a general area of complaint that is causing the patient 130 discomfort or pain. More specifically, in an embodiment described with reference to FIG. 1, the patient 130 may identify the chest as a general area of discomfort or pain. In some embodiments, a patient-identified area of complaint may be associated by a practitioner 122 with an associated or complimentary area of injury which may then be designated as a treatment area. In such an embodiment, the practitioner 122 may apply the stationary electrode 113 within the general area of complaint or treatment area, and initially instruct the amplitude-modulated pulsed DC electrotherapy signal generator 110 to produce a pre-diagnostic electrical signal having an amplitude (e.g., at or below one Volt) relatively lower than that routinely used during therapeutic physical manipulation. The practitioner 122 in such an embodiment may then apply the pre-diagnostic electrical signal to the patient's general area of complaint or treatment area via the electrode 113, and via contact between the electrotherapy glove 120 and a portion of the patient's skin within the general area of complaint or treatment area, causing the patient's musculature or soft tissue to conduct the pre-diagnostic electric signal between the electrotherapy glove 120 and the electrode 113. The practitioner 122 in an embodiment may then slowly increase the amplitude (e.g., voltage) of the applied electrical signal until the patient reports, or the practitioner observes a mild contraction or twitch of the patient's musculature, under, between, or surrounding the electrotherapy glove 120 and the electrode 113 or directly beneath the electrotherapy glove 120. In an embodiment, a signal may be when a first mild contraction or twitch is detected, but it is understood that in not all cases must a first contraction or twitch be detected or observed. This observation may indicate an amplitude (e.g. voltage) the practitioner may use to instruct the amplitude-modulated pulsed DC electrotherapy signal generator 110 to generate a diagnostic electrical signal. The practitioner 122 may use such a diagnostic electrical signal to more specifically identify a physical manipulation target region 131 that may be treated to address the patient's discomfort or pain within the general area of complaint or treatment area.

The practitioner 122 in an embodiment may identify a specific physical manipulation target region 131 in an embodiment by gauging the level of a patient's pain or discomfort during application of the diagnostic electrical signal (e.g., having an amplitude sufficient to produce muscle contraction) across various points within the patient's 130 general area of complaint or treatment area. For example, the practitioner 122 in an embodiment may sweep the electrotherapy glove 120 or specific electrodes within the electrotherapy glove 120 (e.g., as described in greater detail with respect to FIG. 2) across several locations on the patient's 130 upper torso if the patient is complaining of discomfort or pain or the treatment area is within the chest area. In such an embodiment, the practitioner 122 may instruct the patient 130 to indicate when application of the diagnostic electrical signal via the electrode 113 and the electrotherapy glove 120 produce a sensation of pain having an intensity of about seven on a pain scale (e.g., from one to ten on a minimum to maximum scale). A physical manipulation target region 131 in an embodiment may be identified by locating such an area or point where application of the diagnostic electrical signal at the amplitude capable of producing muscle contraction produces a pain or discomfort sensation in the patient 130 having an intensity of seven out of ten in some example embodiments. Other threshold levels may be used in other embodiments. In some embodiments, as described in greater detail with respect to FIGS. 7A, 7B, 8A, and 8B, identification of the area in which the diagnostic electrical signal produces a pain response of roughly seven out of ten in the patient may indicate a physical manipulation target region 131 located separately or relatively distantly from the location of the pain response. In such embodiments, the diagnostic electrical signal may be identifying a trigger point or referred pain associated with an injury in a different location as the target region 131. In such a way, the amplitude-modulated pulsed direct current electrotherapy system may allow a practitioner to locate a physical manipulation target region 131 for electrotherapy-assisted physical manipulation of a patient's musculature using an electrotherapy glove in an embodiment.

Upon identification of the physical manipulation target region 131 in an embodiment, the practitioner 122 may perform electrotherapy-assisted physical manipulation treatment of the patient's musculature or soft tissue within the physical manipulation target region 131. For example, the practitioner 122 may determine an amplitude and frequency of a therapeutic pulsed DC electrical signal underlying an amplitude-modulated pulsed DC treatment electrical signal to apply to the patient 130 within the physical manipulation target 131 region via the electrotherapy glove 120. The practitioner 122 in an embodiment may choose a frequency anywhere between one and 1,000 Hz for the therapeutic pulsed DC primary electrical signal. In a specific embodiment, the therapeutic DC electrical signal may produce pulses of voltage (e.g., between one and five Volts) at a frequency of around 500 Hz (e.g., between 425 and 575 pulses per second).

In some embodiments, the amplitude of the therapeutic pulsed DC electrical signal may be the same as the amplitude of the pulsed DC electrical signal underlying the diagnostic electrical signal. In other embodiments in which the electrotherapy glove is not used for diagnostic purposes, the practitioner 122 may determine the amplitude for the therapeutic pulsed DC electrical signal in a similar fashion as the determination of the pulsed DC electrical signal underlying the diagnostic electrical signal amplitude described herein. More specifically, the practitioner 122 in such embodiments may initially instruct the amplitude-modulated pulsed DC electrotherapy signal generator 110 to produce an electrical signal including an AC electrical signal mixed with a therapeutic pulsed DC electrical signal having an amplitude (e.g., at or below one Volt) relatively lower than that routinely used during therapeutic physical manipulation. The practitioner 122 in such an embodiment may then apply this electrical signal to the patient's physical manipulation target region 131 via the electrotherapy glove 120 and slowly increase the amplitude (e.g., voltage) of the underlying pulsed DC electrical signal until the patient reports, or the practitioner observes a contraction of the patient's musculature within the physical manipulation target region 131. This observation may indicate the amplitude (e.g. voltage) of a therapeutic pulsed DC electrical signal that may be mixed with an AC electrical signal (e.g., as described below with respect to FIG. 6) to generate the amplitude-modulated pulsed DC therapeutic electrical signal.

The type of physical manipulation performed by the practitioner 122 within the patient's physical manipulation target region 131 in an embodiment may depend upon the location of the patient's physical manipulation target region 131, the type of injury the patient 130 has sustained, or whether the patient's 130 pain is referred or local to the injury, among other factors, as described in greater detail with respect to FIGS. 7A, 7B, 8A, and 8B, below. The electrotherapy glove 120 in an embodiment may deliver the amplitude-modulated pulsed DC therapeutic electrical signal through the one or more electrodes situated at various locations along the exterior surface of the electrotherapy glove 120 (e.g., as described in greater detail with respect to FIG. 2), or through electrically conductive fibers interwoven within the exterior surface of the electrotherapy glove 120. The amplitude-modulated pulsed DC therapeutic electrical signal so applied in an embodiment may cause the patient's muscles within the physical manipulation target region 131 to relax, without causing any painful or stinging sensations within the patient's soft tissues or skin, due to the mixing of the therapeutic pulsed DC electrical signal which causes muscle relaxation, and the AC electrical signal which blocks the flow of ions or ion accumulation causing painful or stinging sensations. Such electrotherapy-assisted physical manipulation using the amplitude-modulated pulsed DC electrical signal may decrease unconscious muscle contraction or tensing during physical manipulation treatment, allowing the practitioner 122 to access deeper into muscle tissue within the physical manipulation target region 131 for more in-depth physical manipulation of injured, overworked, or weakened muscles. Such in-depth manipulation may promote quicker healing and more effectively decrease acute or chronic pain associated with muscular or soft tissue injury. In such a way, the amplitude-modulated pulsed direct current electrotherapy system may allow a practitioner 122 to manipulate a patient's 130 tissue made more accessible due to muscle relaxation resulting from application of the electrotherapy via an electrotherapy glove 120 worn by the practitioner 122 during such physical manipulation.

Figure 2:
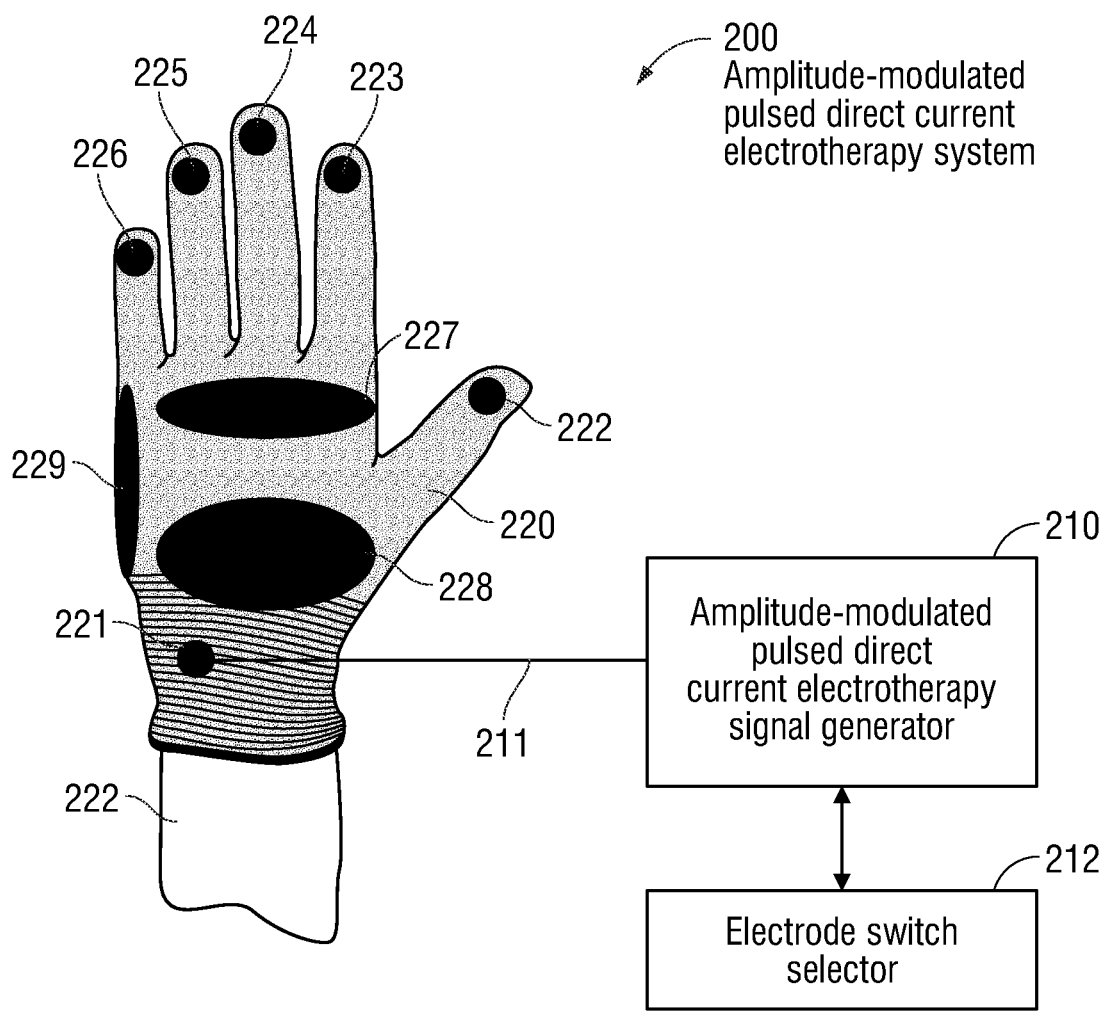
FIG. 2 is a graphical diagram illustrating an amplitude-modulated pulsed DC electrotherapy system according to an embodiment of the present disclosure.

FIG. 2 is a graphical diagram illustrating an amplitude-modulated pulsed direct current (DC) electrotherapy system 200 including a signal generator 210 transmitting an amplitude-modulated pulsed DC electrical signal to an electrotherapy glove 220 according to an embodiment of the present disclosure. As described herein, an amplitude-modulated pulsed DC electrical signal in an embodiment may be applied to a patient during physical manipulation of a patient's musculature or soft tissues (e.g., manual therapy) by a practitioner via an electrotherapy glove 220 worn by the practitioner 222, or during diagnosis or location of a physical manipulation target region on a patient. Such an electrotherapy glove 220 may comprise a portion of an amplitude-modulated pulsed direct current electrotherapy system 200 that further includes an amplitude-modulated pulsed direct current electrotherapy signal generator 210 and a stationary electrode (e.g., as described at 113 of FIG. 1) applied directly to a patient. The electrotherapy glove 220 may include an outer patient contact surface on any portion of the electrotherapy glove 220 to administer the amplitude-modulated pulsed direct current electrotherapy signal according to embodiments herein. The amplitude-modulated pulsed direct current electrotherapy signal generator 210 in an embodiment may transmit an amplitude-modulated pulsed DC electrical signal, which may be described in greater detail with respect to FIG. 6, below, to a port 221 of the electrotherapy glove 220 via an electrically conductive wire or cable 211 the outer patient contact surface of the glove at any portion or to connect to one or more particularly located electrodes (e.g., 222, 223, 224, 225, 226, 227, 228, or 229). As described below, the port 221 may incorporate a microcontroller or programmable integrated circuit in some embodiments to receive instructions from an electrode-switching controller of the amplitude-modulated pulsed DC electrical signal generator 210.

The electrotherapy glove 220 in an embodiment may deliver the amplitude-modulated pulsed DC electrical signal, the pre-diagnostic electrical signal, or the diagnostic electrical signal (e.g., described in greater detail with respect to FIG. 9) to a patient's skin through the outer patient contact surface of the electrotherapy glove 220 such as through electrically conductive fibers interwoven within the exterior surface of the electrotherapy glove 220 and operably connected to the port 221 or via one or more electrodes (e.g., 222, 223, 224, 225, 226, 227, 228, or 229) situated at various particular locations along the exterior surface of the electrotherapy glove 220. Electrodes (e.g., 222, 223, 224, 225, 226, 227, 228, or 229) may be placed along the exterior of the electrotherapy glove 220 at positions relative to the practitioner's hand commonly used in various physical manipulation techniques. For example, electrode 222 may be placed on the pad of the thumb, electrode 223 may be placed on the pad of the index finger, electrode 224 may be placed on the pad of the middle finger, electrode 225 may be placed on the pad of the ring finger, or electrode 226 may be placed on the pad or exterior edge of the pinky finger of the practitioner 222. In another example, an electrode 227 may be placed on the top side of the electrotherapy glove at the knuckles that includes one or more joints between the fingers and metacarpals of the practitioner's 222 hand. As yet another example, an electrode 228 may be placed on the heel of the practitioner's 222 palm. In still another example, an electrode 229 may be placed along the exterior edge (e.g., opposite the thumb) of the practitioner's 222 palm. Other embodiments contemplate placement of electrodes in any portion of the electrotherapy glove 220 intended for direct contact with the patient during execution of a physical manipulation technique for physical therapy, manual therapy or chiropractic therapy. Any or all of the electrodes (e.g., 222, 223, 224, 225, 226, 227, 228, or 229) may be included on the electrotherapy glove 220 in various embodiments.

The practitioner in an embodiment may further direct the amplitude-modulated pulsed direct current electrotherapy signal generator 210 to transmit the amplitude-modulated pulsed DC electrical signal to a specific electrode (e.g., 222, 223, 224, 225, 226, 227, 228, or 229) or combination thereof on the electrotherapy glove 220, or to transmit the signal through all electrodes (e.g., 222, 223, 224, 225, 226, 227, 228, or 229) or through an interwoven electrically conductive fabric simultaneously in various embodiments. For example, and as described in greater detail with respect to FIG. 3 below, the practitioner may use the amplitude-modulated pulsed DC electrotherapy signal generator 210 to select one or more of the electrotherapy glove electrodes (e.g., 222, 223, 224, 225, 226, 227, 228, or 229), or a combination thereof to emit the amplitude-modulated pulsed DC electrical signal. More specifically, the practitioner in an example embodiment may select (e.g., via one or more buttons or through manipulation of a user interface on the amplitude-modulated pulsed DC electrotherapy signal generator 210) to emit the amplitude-modulated pulsed DC electrical signal through the electrode 228 corresponding to the heel of the practitioner's palm. As another example embodiment, the practitioner may select to emit the amplitude-modulated pulsed DC electrical signal through the electrodes 223, 224, 225, and 226 corresponding to the practitioner's fingertips or via the knuckles at 227. In still another example embodiment, the practitioner may select to emit the amplitude-modulated pulsed DC electrical signal through the electrodes 222, 223, and 224 corresponding to the practitioner's thumb and tips of the practitioner's index and middle fingers. These are only a few examples of selections that may be made for specific electrodes within the electrotherapy glove 220, and all possible combinations of electrodes operably connected to the port 221 are also contemplated herein.

In some embodiments, the port 221 may incorporate a microcontroller or programmable integrated circuit capable of receiving instructions identifying practitioner-selected electrodes from a controller or processor of the amplitude-modulated pulsed DC electrical signal generator 210. As described in greater detail below with respect to FIG. 3, the amplitude-modulated pulsed DC electrical signal generator may receive input from a practitioner selecting an electrode or combination of electrodes situated along the exterior of the electrotherapy glove to deliver an amplitude-modulated pulsed DC electrical signal. The amplitude-modulated pulsed DC electrical signal generator in an embodiment may transmit an instruction to a controller within the electrotherapy glove port 221 or to an electrode switch selector 212 to deliver the amplitude-modulated pulsed DC electrical signal only to the practitioner-selected electrodes. In another embodiment, the port 221 may incorporate a plurality of electrically isolated ports, each operably connected to a separate electrode (e.g., 222, 223, 224, 225, 226, 227, 228, or 229) of the electrotherapy glove 220. In such an embodiment, a microcontroller or processor of the amplitude-modulated pulsed DC electrical signal generator or an electrode switch selector 212 may deliver the amplitude-modulated pulsed DC electrical signal only to those electrically isolated ports associated with the practitioner-selected electrodes. The electrode switch selector 212 shown between the amplitude-modulated pulsed DC electrotherapy signal generator 210 and the electrotherapy glove 220 and port 221 may be located at an amplitude-modulated pulsed DC electrotherapy signal generator 210 in some embodiments or in other embodiments the electrode switch selector 212 may be a selectable switch located on the electrotherapy glove 220. In other words, electrode switch selector 212 may be disposed along electrically conductive wire or cable 211, which may comprise a bundle of cables for plural electrodes, at any point from the electrotherapy glove at port 221 to a source location in the amplitude-modulated pulsed DC electrotherapy signal generator 210.

Figure 3:
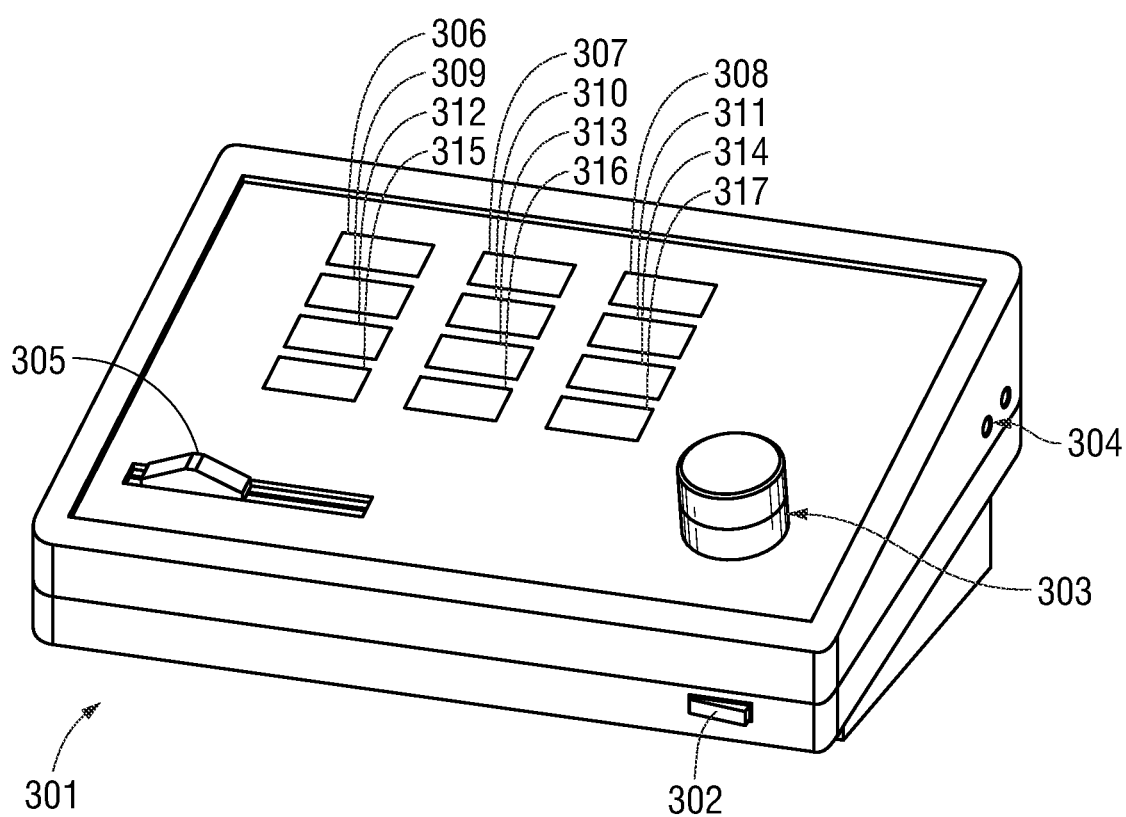
FIG. 3 is a graphical diagram illustrating an amplitude-modulated pulsed direct current electrotherapy signal generator according to an embodiment of the present disclosure.

FIG. 3 is a graphical diagram illustrating an amplitude-modulated pulsed direct current electrotherapy signal generator for transmitting an amplitude-modulated pulsed DC electrical signal to an electrotherapy glove during physical manipulation of a patient's musculature by the electrotherapy glove according to an embodiment of the present disclosure. The amplitude-modulated pulsed direct current electrotherapy signal generator 301 may be powered in an embodiment using standard 120V 60 Hz AC power via an external wall-mount power supply, a portable battery power source, or internal AC-to-DC conversion. The amplitude-modulated pulsed direct current electrotherapy signal generator 301 in an embodiment may have a master shut-off switch 302 that may be modular in that each channel may be controlled individually through panel-mount controls. Channel outputs 304 in an embodiment may be the sum of two waveforms, a pulsed DC electrical signal and an AC electrical signal, as described in greater detail below with respect to FIG. 6. The fixed electrode and electrotherapy glove operating as a single electrode or having a plurality of electrodes embedded thereon in various embodiments may be operably coupled via conductive wire or cable to the amplitude-modulated pulsed DC electrotherapy signal generator 301 at channel output ports 304.

A knob 303 or other input device such as a slider 305 in an embodiment may be used in order to adjust an amplitude or a frequency of a pulsed DC electrical signal in an embodiment. A digital processor in an embodiment may synthesize the waveforms for output and pass the results through digital-to-analog conversion and amplification stages. The output amplitude cap in an embodiment may perform on the processor, and also be clamped by hardware for redundancy. Firmware developed using development environments MPLAB X and Microchip in parallel with the sourcing of the assembled circuit boards may be used in an embodiment.

In some embodiments, an entire or any portion of the electrotherapy glove may be a treatment application electrode. The amplitude-modulated pulsed direct current electrotherapy signal generator 301 in other embodiments may further include one or more buttons (e.g., 306, 307, 308, 309, 310, 311, 312, 313, 314, 315, 316, or 317), switches, or other user interface devices that allow the practitioner to select one or more electrodes embedded within the electrotherapy glove to emit an amplitude-modulated pulsed DC electrotherapy signal. The selection of the one or more buttons (e.g., 306, 307, 308, 309, 310, 311, 312, 313, 314, 315, 316, or 317), switches, or other user interface devices that allow the practitioner to select one or more electrodes may cause an electrode switch selector to select among signal cables and electrodes within or on the external surface of the electrotherapy glove. For example, the practitioner in an embodiment may select button 306 to emit the amplitude-modulated pulsed direct current electrotherapy signal through the electrode on the electrotherapy glove corresponding to the practitioner's thumb (e.g., electrode 222 of FIG. 2). As another example, in an embodiment the practitioner may select button 307 to emit the amplitude-modulated pulsed direct current electrotherapy signal through the electrode on the electrotherapy glove corresponding to the tip of the practitioner's index finger (e.g., electrode 223 of FIG. 2). In another example, the practitioner in an embodiment may select button 308 to emit the amplitude-modulated pulsed direct current electrotherapy signal through the electrode on the electrotherapy glove corresponding to the tip of the practitioner's middle finger (e.g., electrode 224 of FIG. 2). As yet another example, in an embodiment the practitioner may select button 309 to emit the amplitude-modulated pulsed direct current electrotherapy signal through the electrode on the electrotherapy glove corresponding to the tip of the practitioner's ring finger (e.g., electrode 225 of FIG. 2). In still another example, the practitioner in an embodiment may select button 310 to emit the amplitude-modulated pulsed direct current electrotherapy signal through the electrode on the electrotherapy glove corresponding to the tip of the practitioner's pinky finger (e.g., electrode 226 of FIG. 2). As still another example, in an embodiment the practitioner may select button 311 to emit the amplitude-modulated pulsed direct current electrotherapy signal through the electrode on the electrotherapy glove corresponding to the knuckles on the top side portion of the practitioner's hand adjoining the practitioner's fingers and on the top side of the electrotherapy glove (e.g., electrode 227 of FIG. 2). In still another example, in an embodiment the practitioner may select button 312 to emit the amplitude-modulated pulsed direct current electrotherapy signal through the electrode on the electrotherapy glove corresponding to the heel of the practitioner's palm (e.g., electrode 228 of FIG. 2). As yet another example, in an embodiment the practitioner may select button 313 to emit the amplitude-modulated pulsed direct current electrotherapy signal through the electrode on the electrotherapy glove corresponding to the outside of the practitioner's hand (e.g., electrode 229 of FIG. 2).

The practitioner in an embodiment may further direct the amplitude-modulated pulsed direct current electrotherapy signal generator 301 to transmit the amplitude-modulated pulsed DC electrical signal to a combination of electrodes on the electrotherapy glove in various embodiments. For example, and as described in greater detail above with respect to FIG. 2, the practitioner may select button 314 to emit the amplitude-modulated pulsed direct current electrotherapy signal through the electrodes on the electrotherapy glove corresponding to each of the practitioner's fingertips (e.g., electrodes 223, 224, 225, and 226 of FIG. 2). As another example, the practitioner in an embodiment may select button 315 to emit the amplitude-modulated pulsed direct current electrotherapy signal through the electrodes on the electrotherapy glove corresponding to the practitioner's thumb and the tips of the practitioner's index and middle fingers (e.g., electrodes 222, 223, and 224 of FIG. 2). In still another example embodiment, the practitioner in an embodiment may select button 316 to emit the amplitude-modulated pulsed direct current electrotherapy signal through the electrodes on the electrotherapy glove corresponding to the practitioner's entire palm (e.g., electrodes 228 of FIG. 2). As yet another example, the practitioner in an embodiment may select button 317 to emit the amplitude-modulated pulsed direct current electrotherapy signal through the electrodes on the electrotherapy glove corresponding to all of the electrodes located on the electrotherapy glove (e.g., electrodes 222, 223, 224, 225, 226, 227, 228, and 229 of FIG. 2).

Figure 4:
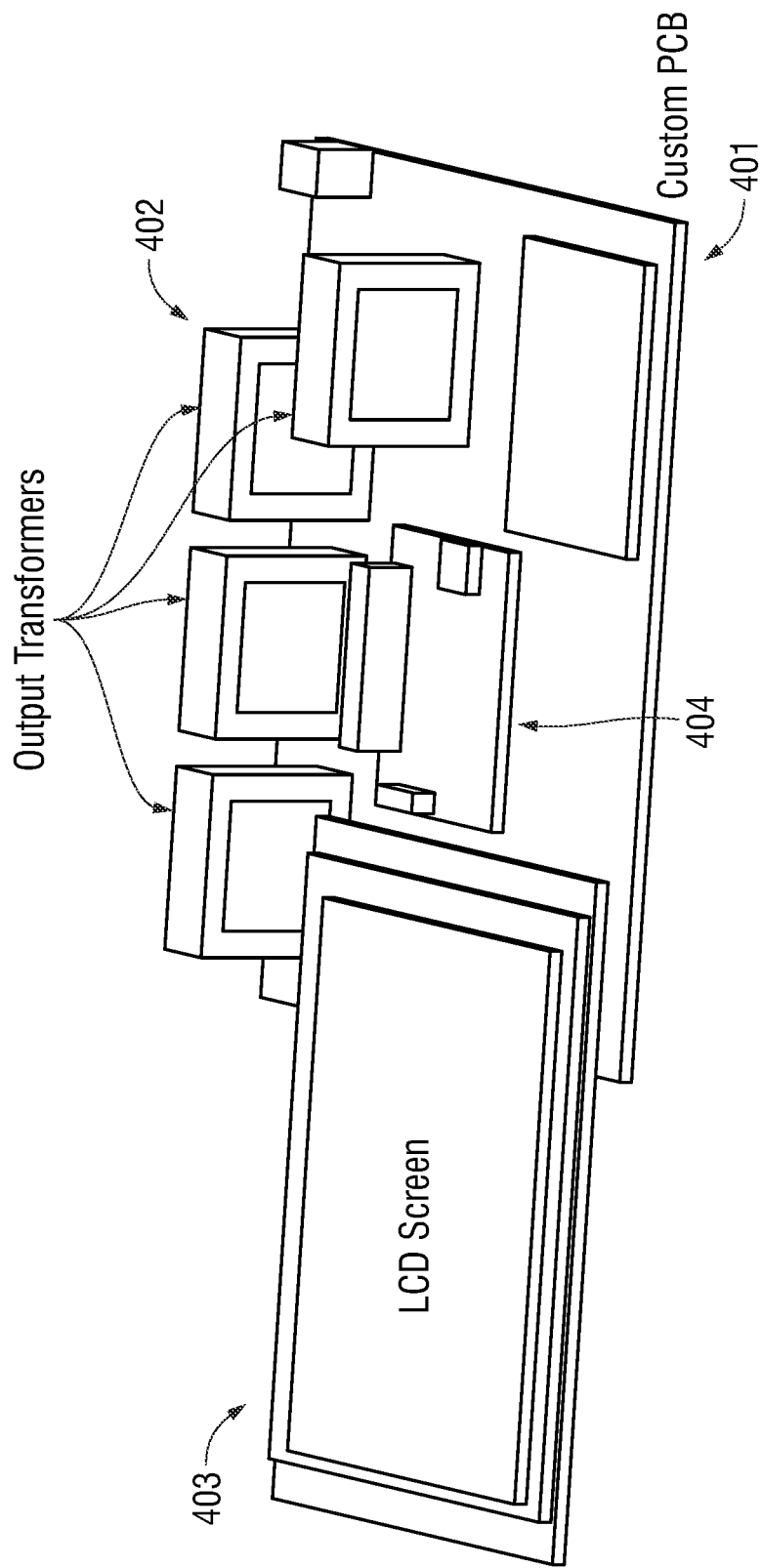
FIG. 4 is a graphical diagram illustrating internal components of an amplitude-modulated pulsed direct current electrotherapy signal generator according to another embodiment of the present disclosure.

FIG. 4 is a graphical diagram illustrating internal components of an amplitude-modulated pulsed direct current electrotherapy signal generator for transmitting an amplitude-modulated pulsed DC electrical signal to an electrotherapy glove during physical manipulation of a patient's musculature by the electrotherapy glove according to an embodiment of the present disclosure. A printed circuit board (PCB) 401 in an embodiment may utilize digital electrical signal synthesis for creation of the amplitude-modulated pulsed direct current electrical signal by routing electrical power through a combination of available infrastructure described in greater detail below with respect to FIG. 5. The power stage in an embodiment may consist of an audio amplifier driving output transformers 402 in FIG. 4 which may isolate the user electrodes from the digital electronics, earth ground, and input power. This stimulation topology in an embodiment may offer a wide range of possibilities regarding electrical signal frequency, amplitude, and mixture, input power requirements, and output power levels, lending to efficient design of instruments meeting varying application requirements. For example, electrical signal frequency, amplitude, and mixture can be changed in firmware by simply reprogramming the device. Output power can be adjusted by either scaling the amplitude of the synthesized electrical signal, or by reducing the amplification of the audio amplifier. LCD screen 403 and corresponding LCD internal components can be programmed to offer various pictures of electrode placements on the bodies or videos of various exercise movements that correspond with various exercises and routines consistent with descriptions in this disclosure.

Controller 404 in an embodiment may operate as a microcontroller, processor (e.g., central processing unit (CPU)), or programmable chip (ASIC) capable of directing operation of a corresponding port or controller incorporated within an operably connected electrotherapy glove. Controller 404 may further include an electrode switch selector switch to select among plural cables or wires corresponding to one or more electrodes within or on the surface of the electrotherapy glove in some embodiments. Such a controller 404 in such an embodiment may receive input from a practitioner (e.g., as described above with respect to FIG. 3 through selection of one or more switches or buttons 306-317) selecting an electrode or combination of electrodes situated along the exterior of the electrotherapy glove to deliver an amplitude-modulated pulsed DC electrical signal. The controller 404 in an embodiment may transmit the amplitude-modulated pulsed DC electrical signal only to ports on the electrotherapy glove operably connected to the selected electrodes. In another embodiment in which the electrotherapy glove incorporates a single port operably connected to the amplitude-modulated pulsed DC electrical signal generator, the controller 404 may transmit an instruction to a controller within the electrotherapy glove and operably connected to that single port to deliver the amplitude-modulated pulsed DC electrical signal only to the selected electrodes via an electrode switch selector located at the electrotherapy glove in some embodiments.

Figure 5:
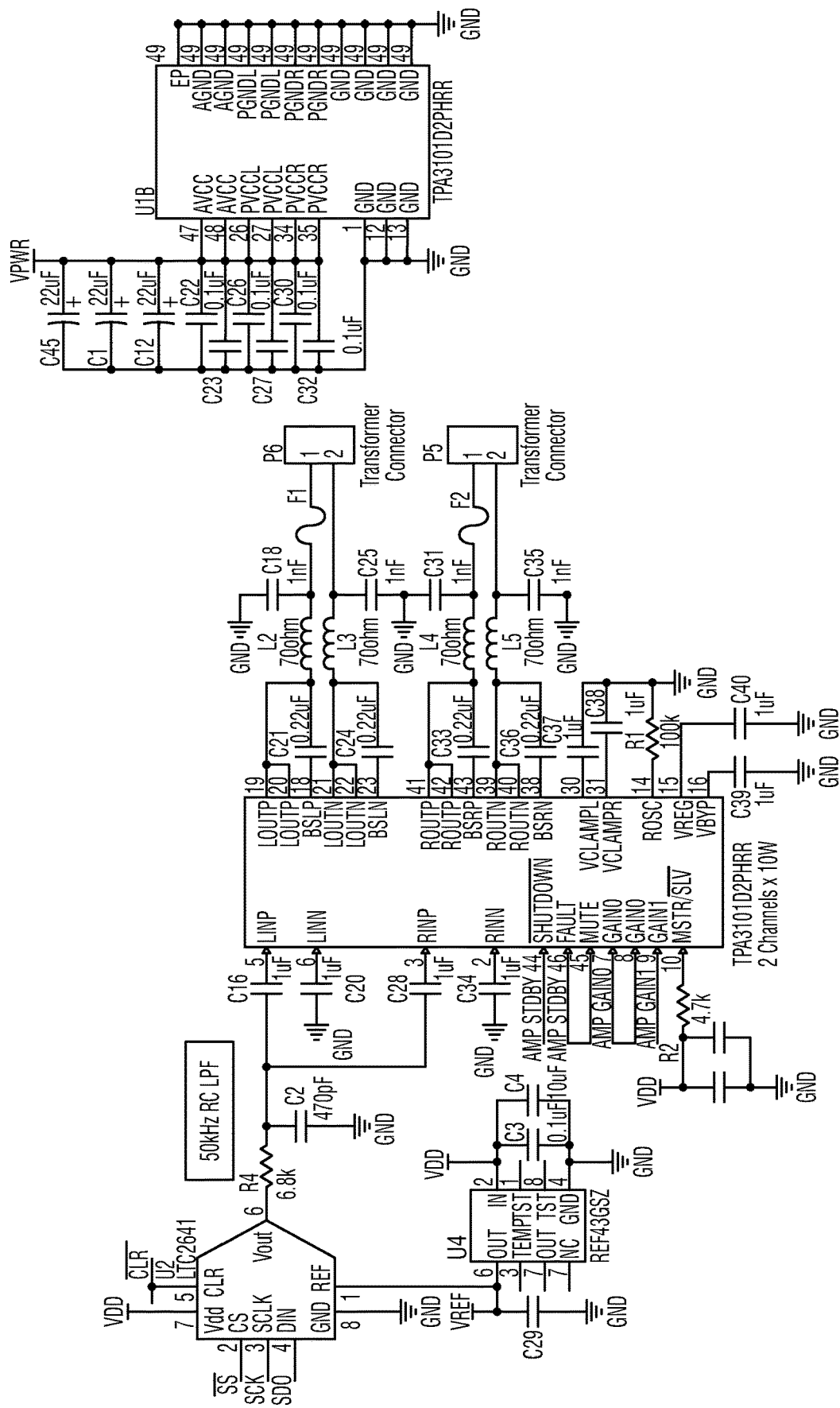
FIG. 5 is a graphical diagram illustrating a circuit schematic for an amplitude-modulated pulsed direct current electrotherapy generator according to an embodiment of the present disclosure.

FIG. 5 is a graphical diagram illustrating a circuit schematic for designing an electrical signal according to an embodiment of the present disclosure. A preliminary circuit schematic is shown in FIG. 5. The schematic drawing illustrates the design of the electrical signal characteristics (e.g., frequency, amplitude) in an embodiment. A microcontroller (not depicted) in an embodiment may control the LTC2641 Digital-to-Analog Converter (DAC) using the Serial Peripheral Interface (SPI) bus standard. The electrical signal created by the DAC in an embodiment may pass through a low-pass RC filter and then A/C coupled into both input channels of a stereo audio amplifier. Amplifier output, gain, and fault conditions in an embodiment may be controlled and monitored by the microcontroller. The output of each audio amplifier channel may pass through an EMI filter in an embodiment and a fuse before being connected to one side of the output transformer through connectors P5 and P6. Electrodes in an embodiment may be connected to the opposite side of the output ports that are connected to the transformers. The microcontroller may control switching among electrodes.

While an example of suitable hardware is provided above, the invention is not limited to being implemented in any particular type of hardware. Further, it should be recognized that embodiments of the present invention can be implemented via computer hardware or software, or a combination of both. The methods in various embodiments described herein may be implemented in computer programs using standard programming techniques-including a computer-readable storage medium configured with a computer program, where the storage medium so configured causes a computer to operate in a specific and predefined manner-according to the methods and figures described in embodiments of this specification. Each program in an embodiment may be implemented in a high-level procedural or object-oriented programming language to communicate with a computer system. However, the programs in various embodiments may be implemented in assembly or machine language, if desired. In any case, the language in an embodiment may be a compiled or interpreted language. Moreover, the program may run on dedicated integrated circuits programmed for that purpose in an embodiment.

Further, methodologies in various embodiments described herein may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein may include these and other various types of computer-readable storage media when such media contain instructions or programs for implementing the steps described above in conjunction with a microprocessor or other data processor. The invention may also include the computer itself when programmed according to the methods and techniques described herein.

Computer programs in various embodiments described herein may be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display. Further, throughout the present specification, discussions utilizing terms such as "calculating," "determining," "measuring," "generating," "detecting," "forming," or the like, also may refer to the action and processes of a computer system, or similar electronic device, that manipulates and transforms data represented as physical quantities within the computer system into other data similarly represented as physical quantities within the computer system or other information storage, transmission or display devices.

Figure 6:
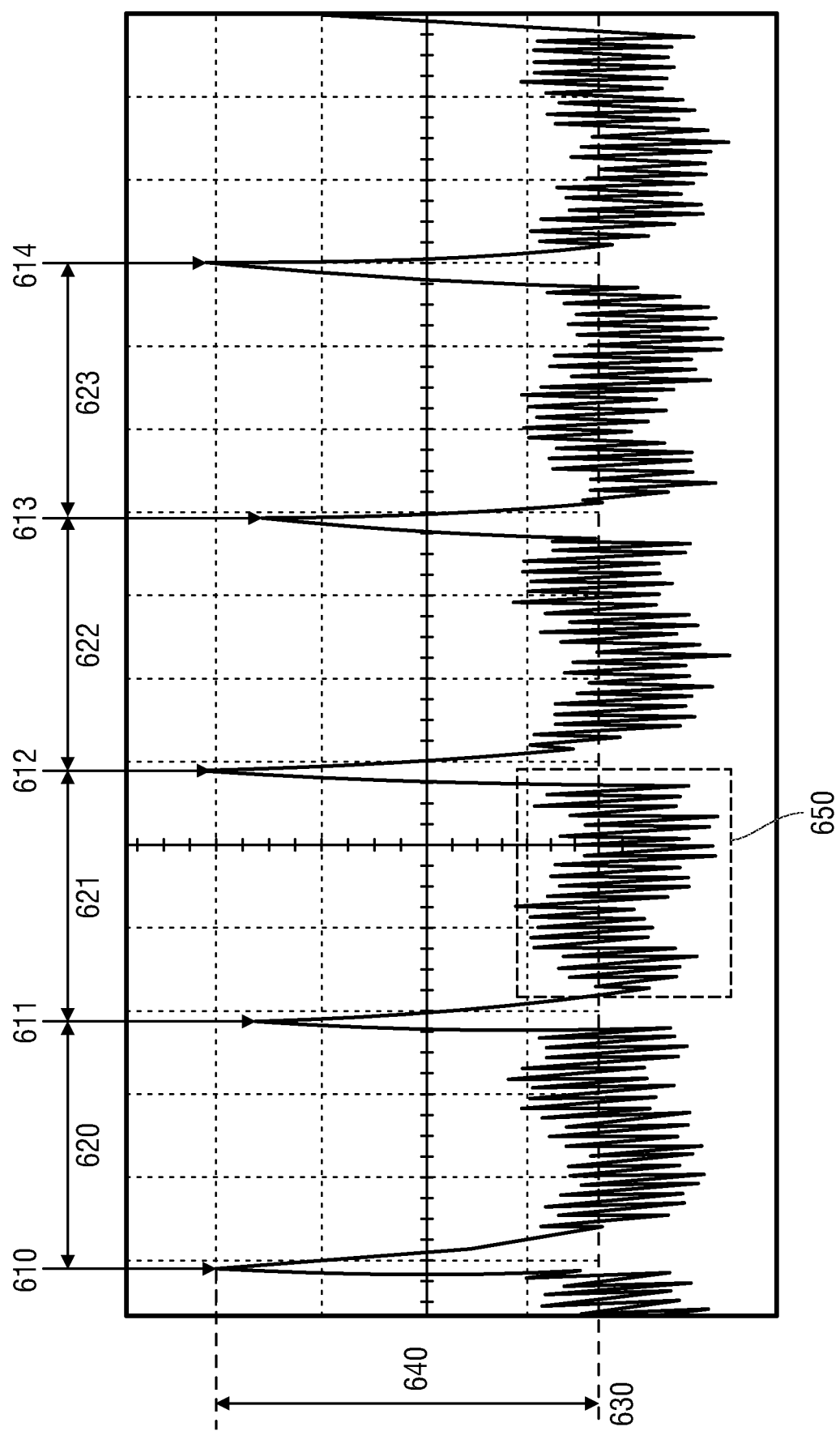
FIG. 6 is a graphical diagram illustrating an amplitude-modulated pulsed DC electrical signal according to an embodiment of the present disclosure.

FIG. 6 is a graphical diagram illustrating an amplitude-modulated pulsed DC electrical signal formed by mixing a pulsed DC electrical signal and an AC electrical signal according to an embodiment of the present disclosure. The amplitude-modulated pulsed DC electrical signal displayed at FIG. 6 may be used for pre-diagnostic, diagnostic, or therapeutic purposes (e.g., as described above with respect to FIG. 1, and below with respect to FIGS. 9 and 10) in various embodiments. As described herein, existing electrotherapy systems apply an electrical current to a patient's musculature or soft tissue via one or more electrodes or similar structures placed in contact with a patient's skin. Many existing systems apply a pulsed DC electrical signal because DC signals pulsed at high frequencies (e.g., 100 to 1000 Hz) have been shown to decrease muscle contraction. However, such DC signals may cause a Faradaic reaction within the patient's skin or adipose tissue situated nearby or in contact with the electrode delivering the DC signal, in which charged particles (e.g., electrons or ions) transfer across the electrode and into the patient's skin or tissue. These ions may then reduce or oxidize to another species, which may further cause a patient to experience a prickling, hot, or painful sensation at the site of application. Some existing electrotherapy systems have adapted to this obstacle by employing an AC signal, rather than a DC signal. Alternating current signals inhibit the transfer of charged particles across the electrode and into the patient's skin or adipose tissue. Thus, application of an AC signal decreases or inhibits the prickling, hot, or painful sensations felt by patients during application of direct current. However, AC signals of the same frequencies (e.g., 100 to 1000 Hz) used in application of DC signals have been shown to cause muscle contraction, rather than the muscle relaxation caused by application of DC signals.

The amplitude-modulated pulsed DC current electrotherapy system in an embodiment may generate an amplitude-modulated pulsed DC electrical signal comprising a pulsed DC electrical signal mixed with an AC signal to attain the benefits of each. The pulsed DC electrical signal may include pulses 610, 611, 612, 613, and 614 of peak amplitude 640 (e.g., between 4 and 5 Volts) occurring at regular intervals (e.g., 620, 621, 622, 623, respectively) preset by the practitioner according to a determined pulsed DC electrical signal frequency (e.g., as described above with respect to FIG. 1). For example, the pulsed DC electrical signal in an embodiment may be pulsed at a frequency (e.g., between one and 1,000 Hz) high enough to cause muscle relaxation. More specifically, the pulsed DC electrical signal in an embodiment may have a frequency between 100 Hz and 1000 Hz or pulses per second.

An AC signal may be superimposed or mixed with this pulsed DC electrical signal in embodiments described herein in order to inhibit the transfer of charged particles across electrodes carrying the signal and applied to the patient. The AC signal may cause amplitude-modulation of the amplitude-modulated pulsed DC electrical signal between each of the pulses 610, 611, 612, 613, and 614 in an embodiment, as shown within box 650. The AC signal may have an amplitude magnitude anywhere between zero and one Volt. In some embodiments, as shown in FIG. 6, the amplitude of the AC signal may vary between a positive and negative value, with the median amplitude at zero volts (e.g., between negative 0.5 Volts and positive 0.5 Volts). The AC signal may have a frequency relatively higher than the frequency of the pulsed DC electrical signal in an embodiment. For example, the AC signal may have a frequency anywhere between one and 1,000 KHz, as compared to the frequency range of one to 1,000 Hz (or 0.001 and one KHz) for the pulsed DC electrical signal. In a specific embodiment, the AC signal may have a frequency of 40 KHz and the pulsed DC electrical signal may have a frequency of 450 Hz.

This combined or mixed signal that includes both the pulsed DC electrical signal and an AC signal may cause relaxation of the patient's muscles while avoiding the prickling, hot, or painful sensations caused by application of DC current alone. Mixing of the AC signal with the DC electrical signal in such a way may effectively modulate the amplitude (e.g., describing total voltage from both the underlying pulsed DC electrical signal and the AC signal) of the pulsed DC electrical signal, resulting in an amplitude-modulated pulsed DC electrical signal.

Figure 7A:
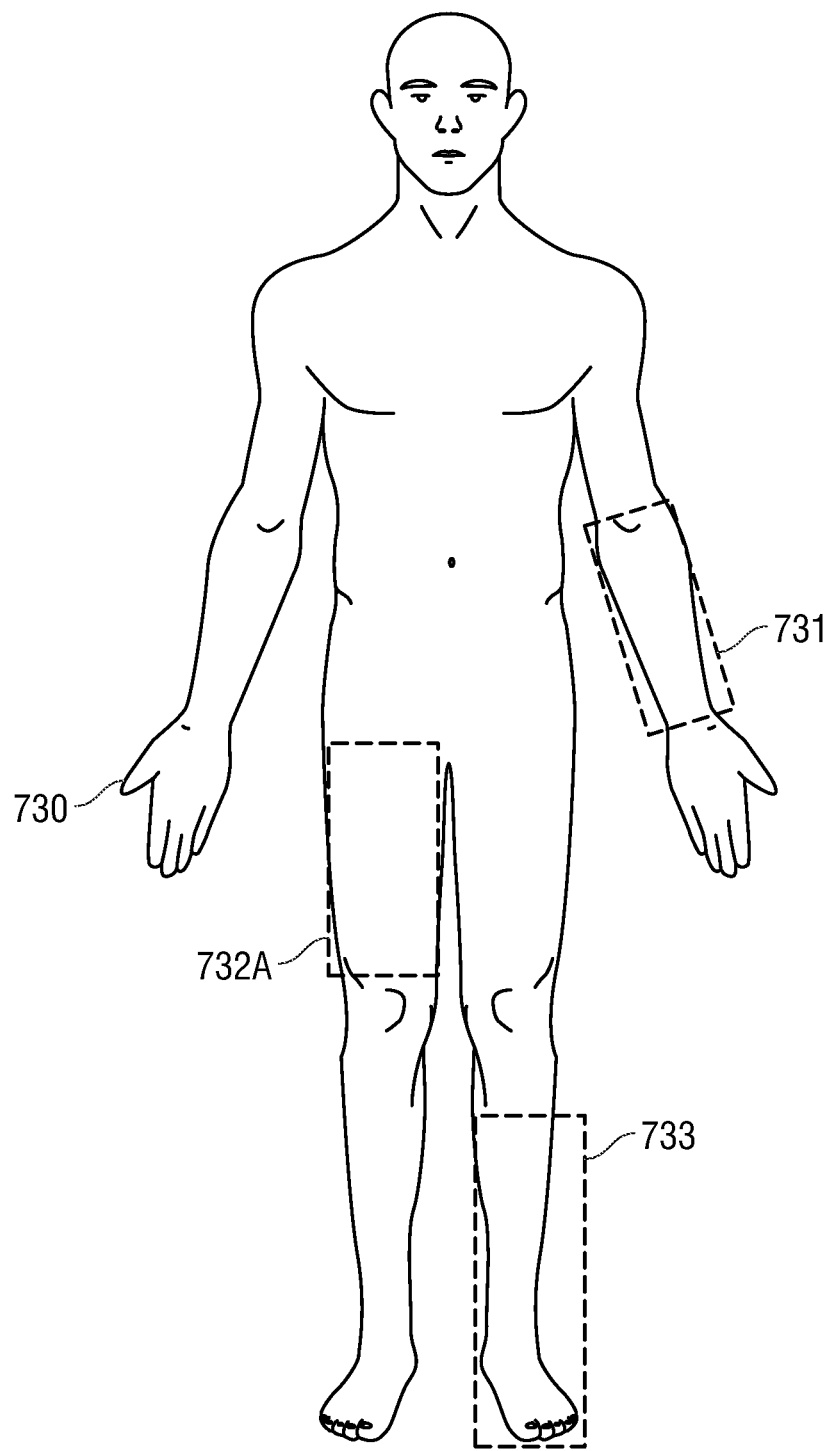
FIG. 7A is a front-view graphical diagram illustrating areas of complaint according to an embodiment of the present disclosure.

FIG. 7A is a front-view graphical diagram illustrating areas of complaint, or practitioner-estimated area of treatment on a patient according to an embodiment of the present disclosure. As described herein, a practitioner may use an electrotherapy glove to identify or diagnose a physical manipulation target region of a patient's musculature or soft tissue. For example, an electrotherapy-assisted physical manipulation session in an embodiment may begin with a patient 730 identifying a general area of complaint that is causing the patient 730 discomfort or pain, or the practitioner may identify an area estimated for treatment. More specifically, the patient 730 or practitioner in an embodiment may identify the forearm area 731 as the general area of complaint or treatment area. In another embodiment, the patient 730 or practitioner may identify the thigh 732A as the general area of complaint or treatment area. In still another embodiment, the patient or practitioner may identify the lower leg 733, including the shin, foot, or upper ankle as the general area of complaint or treatment area.

The practitioner in various embodiments may use the electrotherapy glove, as described in greater detail with respect to FIG. 1, above, to apply a diagnostic electrical signal to identify one or more physical manipulation target regions associated with each general area of complaint or treatment area (e.g., 731, 732A, or 733) that the practitioner may perform manual therapy or physically manipulate in order to address the patient's 730 pain or discomfort within the general area of complaint or treatment area. The practitioner in an embodiment may, for example, identify a specific physical manipulation target region in an embodiment by gauging the level of a patient's muscle response, pain, or discomfort during application of a diagnostic electrical signal (e.g., via the electrotherapy glove) across various points within the patient's 730 general area of complaint or treatment area (e.g., 731, 732A, or 733). A physical manipulation target region (e.g., as described in greater detail with respect to FIGS. 8A and 8B, below) in an embodiment may be identified by locating an area or point where application of the diagnostic electrical signal at the amplitude capable of producing muscle contraction produces a pain or discomfort sensation in the patient 730 having an intensity above the patient's baseline pain or discomfort sensation prior to initiation of the therapy session. Any range of pain or discomfort threshold may be used. In a scale to ten, the pain or discomfort level may be any threshold level such as 3 or above. For example, the physical manipulation target region may be identified by locating an area or point where application of the diagnostic electrical signal to a patient with a baseline pain level of four out of ten produces a pain response of seven out of ten at a hot spot area, or any other threshold level exceeding four out of ten.

In some embodiments, identification of the area in which the diagnostic electrical signal produces a pain response of roughly seven out of ten in the patient may indicate a physical manipulation target region located separately or relatively distantly from the location of the pain response. In such embodiments, the diagnostic electrical signal may be identifying a trigger point or referred pain associated with an injury in a different location. For example, and as described in greater detail with respect to FIGS. 8A and 8B, below, pain within the general area of complaint or treatment area 732A (e.g., thigh pain) may be caused by nerve compression due to inflammation within the lower back. In other words, thigh pain within area 732A may be caused by inflammation at a trigger point within the lower back. In such a case, the practitioner may determine the lower back is the physical manipulation target region for treatment of such thigh pain. In other embodiments, the reverse may be true, for example. In such a way, the amplitude-modulated pulsed direct current electrotherapy system may allow a practitioner to locate a physical manipulation target region for electrotherapy-assisted physical manipulation of a patient's musculature using an electrotherapy glove in an embodiment.

Figure 7B:
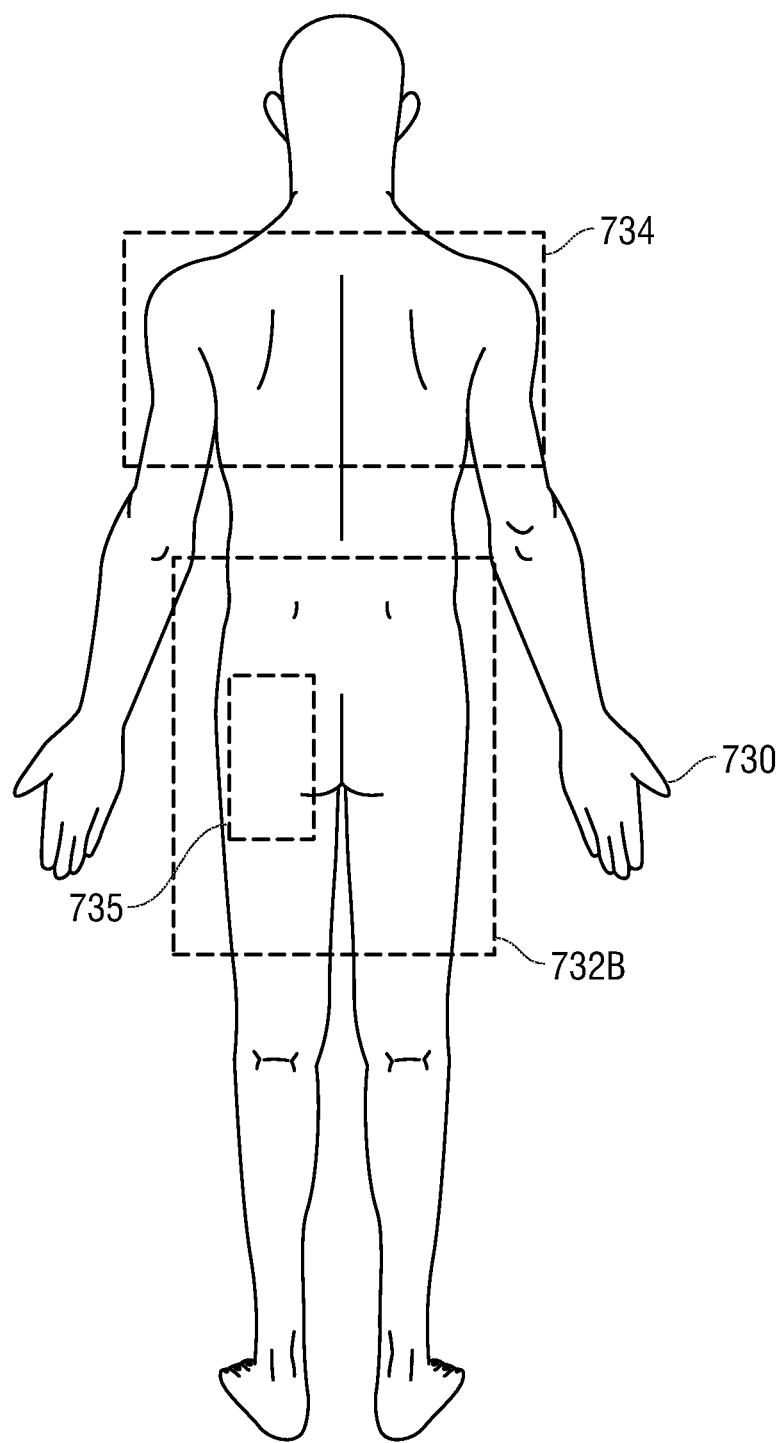
FIG. 7B is a rear-view graphical diagram illustrating areas of complaint according to an embodiment of the present disclosure.

FIG. 7B is a rear-view graphical diagram illustrating areas of complaint on a patient according to an embodiment of the present disclosure. A patient 730 in an embodiment may identify the lower back/upper legs area 732B as the general area of complaint or treatment area. In another embodiment, the patient 730 or practitioner may identify the gluteus muscles 735 as the general area of complaint or treatment area. In still another embodiment, the patient or practitioner may identify the upper back area 734 (e.g., including the neck, shoulders, or upper arms) as the general area of complaint or treatment area.

The practitioner in various embodiments may use the electrotherapy glove, as described in greater detail with respect to FIG. 1, above, to apply a diagnostic electrical signal to identify one or more physical manipulation target regions associated with each general area of complaint or treatment area (e.g., lower back or hamstring area 732B, shoulder/upper back area 734, or gluteal muscle 735) upon which the practitioner may perform manual therapy in order to address the patient's 730 pain or discomfort within the general area of complaint or treatment area. The practitioner in an embodiment may, for example, identify a specific physical manipulation target region in an embodiment by gauging the level of a patient's muscle response, pain, or discomfort during application of a diagnostic electrical signal (e.g., via the electrotherapy glove) across various points within the patient's 730 general area of complaint or treatment area (e.g., lower back or hamstring area 732B, shoulder/upper back area 734, or gluteal muscle 735). A physical manipulation target region (e.g., as described in greater detail with respect to FIGS. 8A and 8B, below) in an embodiment may be identified by locating an area or point where application of the diagnostic electrical signal at the amplitude capable of producing muscle contraction produces a pain or discomfort sensation in the patient 730 having an intensity of seven out of ten, or any other threshold level.

As described herein, in some embodiments, identification of the area in which the diagnostic electrical signal produces a pain response of roughly seven out of ten, or any other threshold level in the patient (e.g., any level above a baseline pain or discomfort level) may indicate a physical manipulation target region located separately or relatively distantly from the location of the pain response. In such embodiments, the diagnostic electrical signal may be identifying a trigger point or referred pain associated with an injury in a different location. For example, and as described in greater detail with respect to FIGS. 8A and 8B, below, pain within the general area of complaint or treatment area 735 (e.g., gluteal pain or gluteal inefficiency) may be caused by nerve compression or inflammation such as due to some type of mechanical force exerted on a nerve within the neck or jaw. In other words, gluteal pain or inefficiency within area 735 may be caused by inflammation at a trigger point within the neck or jaw. In such a case, the practitioner may determine the neck or jaw is the physical manipulation target region for treatment of such gluteal pain or inefficiency.

As another example, pain within the general area of complaint or treatment area 732B (e.g., lower back pain) may be caused by nerve compression or inflammation due to injury, overactivity, or weakness of the psoas muscle, thigh muscles, gluteal muscles, or hamstring. In such a case, the practitioner may determine the psoas muscle or the thigh muscle is the physical manipulation target region for treatment of such lower back pain. In such a way, the amplitude-modulated pulsed direct current electrotherapy system may allow a practitioner to locate a physical manipulation target region for electrotherapy-assisted physical manipulation of a patient's musculature using an electrotherapy glove in an embodiment.

Figure 8A:
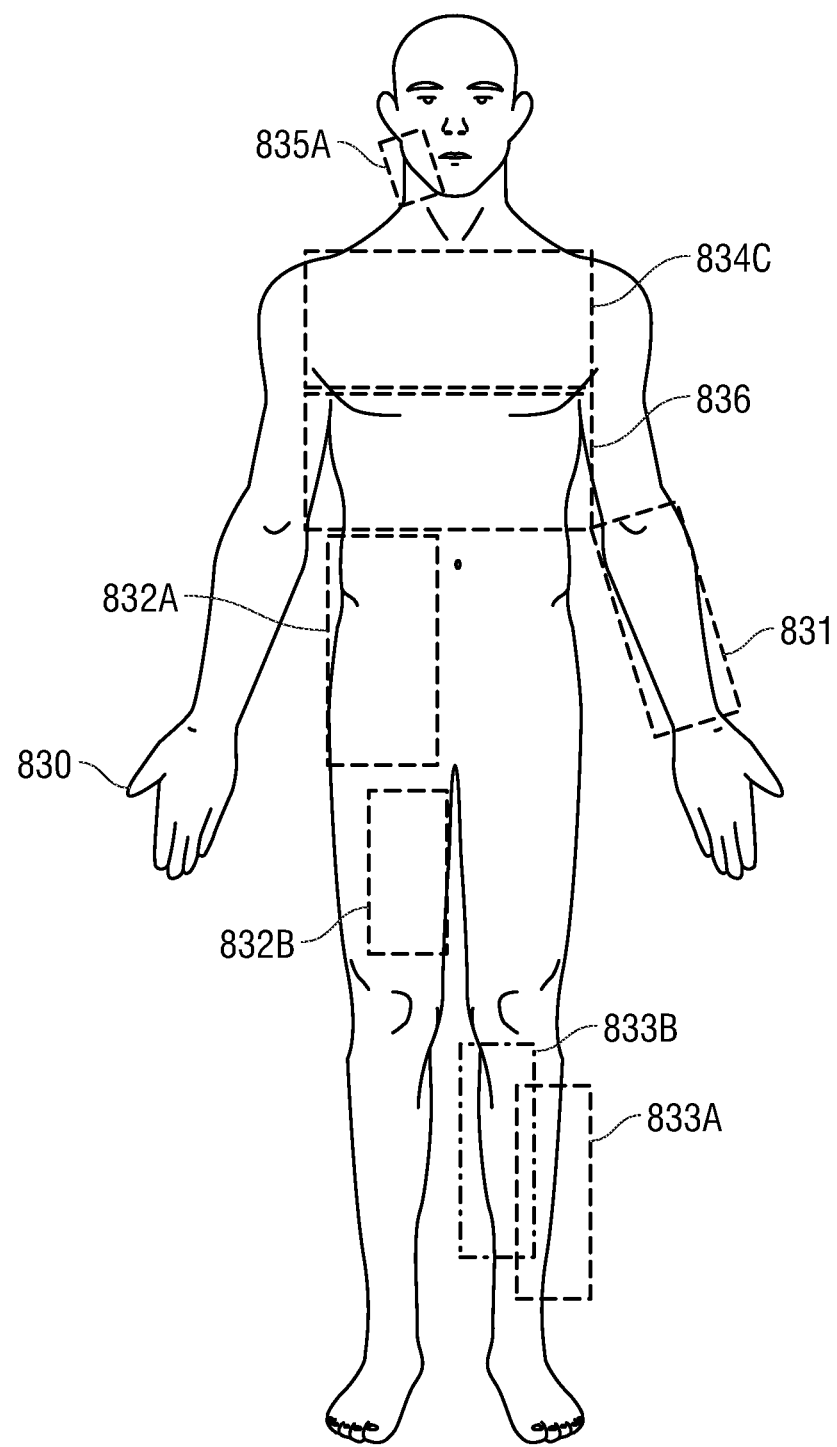
FIG. 8A is a front-view graphical diagram illustrating physical manipulation target regions according to an embodiment of the present disclosure.

FIG. 8A is a front-view graphical diagram illustrating physical manipulation target regions on a patient according to an embodiment of the present disclosure. As described herein, a practitioner in an embodiment may use an electrotherapy glove to perform a physical manipulation of the patient's soft tissue or musculature within a physical manipulation target region during delivery of an amplitude-modulated pulsed DC electrical signal to the electrotherapy glove. In one embodiment, the practitioner may perform such a physical manipulation for global reduction of protective and inhibitory neuromuscular patterns within the patient's entire body. This type of procedure may be performed as a preventative measure, and may not relate to or depend upon the existence of any specific general area of complaint or treatment area from the patient. In such an embodiment, the practitioner may perform an electrotherapy-assisted physical manipulation of the patient's 830 musculature or soft tissue via an electrotherapy glove described herein within the physical manipulation target region 836 of the patient's 830 diaphragm region, or lower rib cage region.

In some embodiments, the physical manipulation target region may be co-located, or overlap the patient's 830 general area of complaint or treatment area, as described in greater detail with respect to FIGS. 7A and 7B above. For example, the practitioner may perform an electrotherapy-assisted physical manipulation of the patient's 830 musculature or soft tissue via an electrotherapy glove described herein within the physical manipulation target region 831 of the patient's forearm in an embodiment in which the patient has identified the forearm as the general area of complaint or treatment area (e.g., as described in FIG. 7A at 731). More specifically, physical manipulation target region 831 in an embodiment may include one or more the brachioradialis or pronator teres muscles. As described in greater detail with respect to FIG. 10, below and with reference to FIG. 2, above, the amplitude-modulated pulsed direct current may also be transmitted to electrodes or fibers of the electrotherapy glove. The electrotherapy glove may have an outer patient contact surface of any portion that may be the treatment electrode in some embodiments. In other embodiments, electrodes in the electrotherapy glove may be situated at the practitioner's fingertips, or at the pad of the thumb (e.g., 222, 223, 224, 225, or 226 as shown in FIG. 2) for physical manipulation of the patient's brachioradialis, or pronator teres musculature with the practitioner's fingers or thumb.

As another example, the practitioner may perform an electrotherapy-assisted physical manipulation of the patient's 830 musculature or soft tissue via an electrotherapy glove described herein within the physical manipulation target region 833A or 833B of the patient's lower leg in an embodiment in which the patient has identified the lower leg as the general area of complaint or treatment area (e.g., as described in FIG. 7A at 733). More specifically, physical manipulation target region 833A may include the fibularis longus muscle and the physical manipulation target region 833B may include the proximal tibialis posterior muscle in an embodiment. As described in greater detail with respect to FIG. 10, below and with reference to FIG. 2, above, the amplitude-modulated pulsed direct current may also be transmitted to electrodes or fibers of the electrotherapy glove. The electrotherapy glove may have an outer patient contact surface of any portion that may be the treatment electrode in some embodiments. In other embodiments, electrodes in the electrotherapy glove may be situated at the practitioner's fingertips, or at the pad of the thumb (e.g., 222, 223, 224, 225, or 226 as shown in FIG. 2) for physical manipulation of the patient's fibularis longus muscle or the tibias posterior muscle with the practitioner's fingers or thumb.

In other embodiments, and as described in greater detail above with respect to FIGS. 7A and 7B, a physical manipulation target region may be located separately or relatively distantly from the location of the pain response. In such embodiments, the diagnostic electrical signal may be used to identify a trigger point or referred pain associated with an injury in a different location. For example, the practitioner may perform an electrotherapy-assisted physical manipulation of the patient's 830 musculature or soft tissue via an electrotherapy glove described herein within the physical manipulation target region 832A of the psoas muscle or 832B of the thigh muscle in an embodiment in which pain within the patient's 830 general area of complaint or treatment area (e.g., the lower back as described in FIG. 7B at 732B) is referred pain caused by injury, inflammation, weakness, or overtaxed psoas or thigh muscles (e.g., quadriceps). More specifically, physical manipulation target region 832A may include the psoas muscle, oblique muscles along the iliac crest, or origin of the iliacus and the physical manipulation target region 832B may include the adductor muscles in an embodiment. As described in greater detail with respect to FIG. 10, below and with reference to FIG. 2, above, the amplitude-modulated pulsed direct current may also be transmitted to electrodes or fibers of the electrotherapy glove. The electrotherapy glove may have an outer patent contact surface of any portion that may be the treatment electrode in some embodiments. In other embodiments, electrodes in the electrotherapy glove may be situated at the practitioner's fingertips, or at the pad of the thumb (e.g., 222, 223, 224, 225, or 226 as shown in FIG. 2) and to electrodes or fibers situated at the heel of the practitioner's palm (e.g., 228) for physical manipulation of the patient's psoas, obliques along the iliac crest, or origin of the iliacus musculature, or of the patient's adductor muscles with the practitioner's fingers, thumb, or heel of palm.

As another example, the practitioner may perform an electrotherapy-assisted physical manipulation of the patient's 830 musculature or soft tissue via an electrotherapy glove described herein within the physical manipulation target region 835A of the jaw muscles in an embodiment in which pain or inefficiency within the patient's 830 general area of complaint or treatment area (e.g., the gluteal muscles as described in FIG. 7B at 735) is caused by injured, inflamed, weak, or overtaxed jaw musculature. More specifically, physical manipulation target region 835A may include the muscles of the jawbone posterior to the temporomandibular joint (TMJ) in an embodiment. As described in greater detail with respect to FIG. 10, below and with reference to FIG. 2, above, the amplitude-modulated pulsed direct current may also be transmitted to electrodes or fibers of the electrotherapy glove. The electrotherapy glove may have an outer patient contact surface of any portion that may be the treatment electrode in some embodiments. In other embodiments, electrodes in the electrotherapy glove may be situated at the practitioner's fingertips, or at the pad of the thumb (e.g., 222, 223, 224, 225, or 226 as shown in FIG. 2) for physical manipulation of the patient's the muscles of the jawbone posterior to the temporomandibular joint (TMJ) with the practitioner's fingers or thumb.

In still another example, the practitioner may perform an electrotherapy-assisted physical manipulation of the patient's 830 musculature or soft tissue via an electrotherapy glove described herein within the physical manipulation target region 834C of the pectoral muscles in an embodiment in which pain within the patient's 830 general area of complaint or treatment area (e.g., the upper back as described in FIG. 7B at 734) is referred pain caused by injured, inflamed, weak, or overtaxed pectoral muscles. More specifically, physical manipulation target region 834C may include the clavicular pectoral muscles or subclavius muscles and soft tissue in an embodiment. As described in greater detail with respect to FIG. 10, below and with reference to FIG. 2, above, the amplitude-modulated pulsed direct current may also be transmitted to electrodes or fibers of the electrotherapy glove. The electrotherapy glove may have an outer patient contact surface of any portion that may be the treatment electrode in some embodiments. In other embodiments, electrodes in the electrotherapy glove may be situated at the practitioner's fingertips, or at the pad of the thumb (e.g., 222, 223, 224, 225, or 226 as shown in FIG. 2) for physical manipulation of the clavicular pectoral muscles or subclavius muscles and soft tissue with the practitioner's fingers or thumb.

Figure 8B:
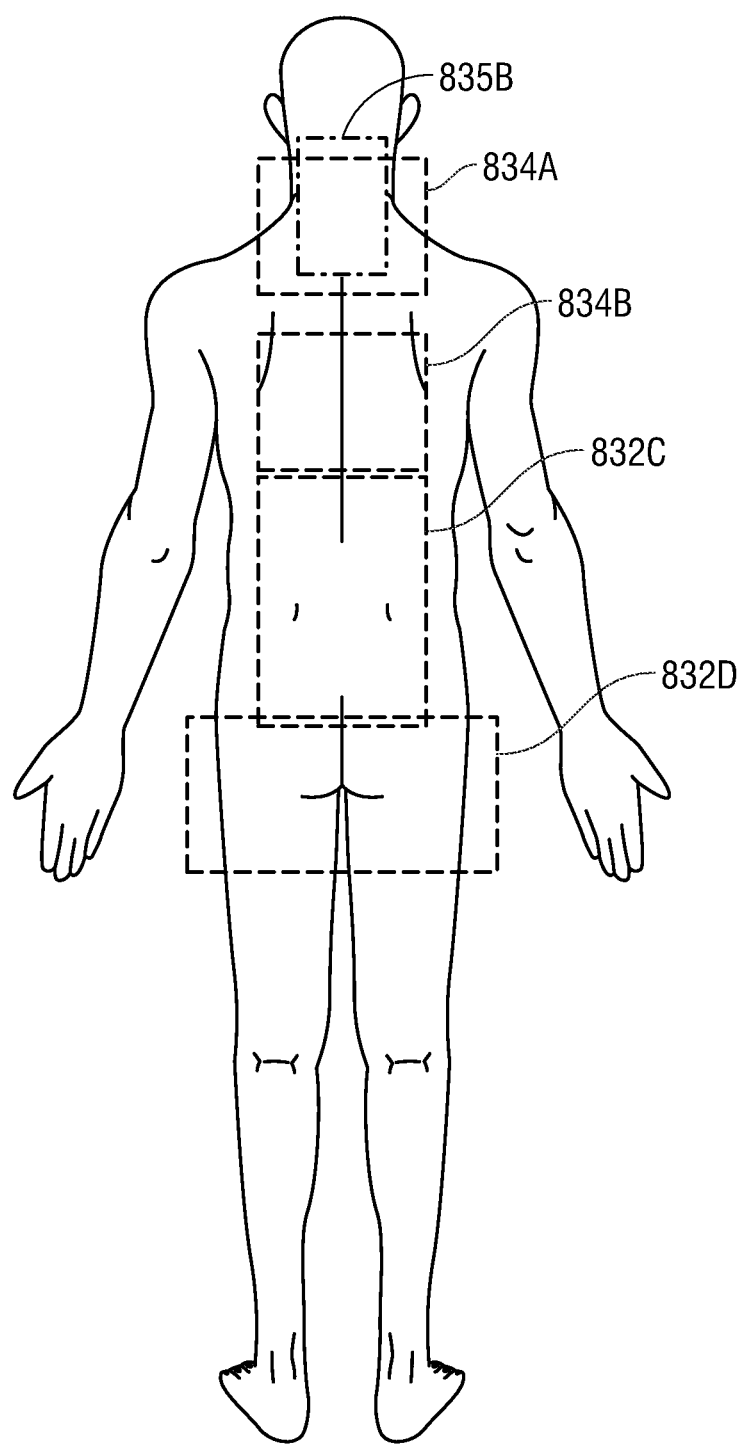
FIG. 8B is a rear-view graphical diagram illustrating physical manipulation target regions according to an embodiment of the present disclosure.

FIG. 8B is a rear-view graphical diagram illustrating physical manipulation target regions on a patient according to an embodiment of the present disclosure. In some embodiments, the physical manipulation target region may be co-located, or overlap the patient's 830 general area of complaint or treatment area, as described in greater detail with respect to FIGS. 7A and 7B above. For example, the practitioner may perform an electrotherapy-assisted physical manipulation of the patient's 830 musculature or soft tissue via an electrotherapy glove described herein within the physical manipulation target region 832C, or 832D of the patient's lower back in an embodiment in which the patient has identified the lower back as the general area of complaint or treatment area (e.g., as described in FIG. 7B at 732B). More specifically, physical manipulation target region 832C in an embodiment may include one or more spinal extensors from the vertebrae from approximately the fifth lumbar (L5) to the sixth thoracic (T6), and the physical manipulation target region 832D may include the anterior segment of the gluteus medius muscle or the tensor fascia latae muscle. As described in greater detail with respect to FIG. 10, below and with reference to FIG. 2, above, the amplitude-modulated pulsed direct current may also be transmitted to electrodes or fibers of the electrotherapy glove. The electrotherapy glove may have an outer patient contact surface of any portion that may be the treatment electrode in some embodiments. In other embodiments, electrodes in the electrotherapy glove may be situated at the practitioner's fingertips, or at the pad of the thumb (e.g., 222, 223, 224, 225, or 226 as shown in FIG. 2) and to electrodes or fibers situated at the heel of the practitioner's palm (e.g., 228) for physical manipulation of the one or more spinal extensors from the vertebrae from the fifth lumbar (L5) to the sixth thoracic (T6), or of the patient's anterior segment of the gluteus medius muscle or the tensor fascia latae muscle with the practitioner's fingers, thumb, or heel of palm.

As another example, the practitioner may perform an electrotherapy-assisted physical manipulation of the patient's 830 musculature or soft tissue via an electrotherapy glove described herein within the physical manipulation target region 834A or 834B of the patient's upper back and neck in an embodiment in which the patient has identified the upper back region as the general area of complaint or treatment area (e.g., as described in FIG. 7B at 734). More specifically, physical manipulation target region 834A may include one or more scalene muscles, and the physical manipulation target region 834B may include spinal extensors from the vertebrae from the first to sixth thoracic (T1 to T6) in an embodiment. As described in greater detail with respect to FIG. 10, below and with reference to FIG. 2, above, the amplitude-modulated pulsed direct current may also be transmitted to electrodes or fibers of the electrotherapy glove. The electrotherapy glove may have an outer patient contact surface of any portion that may be the treatment electrode in some embodiments. In other embodiments, electrodes in the electrotherapy glove may be situated at the practitioner's fingertips, or at the pad of the thumb (e.g., 222, 223, 224, 225, or 226 as shown in FIG. 2) for physical manipulation of the one or more scalene muscles or spinal extensors from the vertebrae from the first to sixth thoracic (T1 to T6) with the practitioner's fingers or thumb.

In other embodiments, and as described in greater detail above with respect to FIGS. 7A and 7B, a physical manipulation target region may be located separately or relatively distantly from the location of the pain response. In such embodiments, the diagnostic electrical signal may be used to identify a trigger point or referred pain associated with an injury in a different location. For example, the practitioner may perform an electrotherapy-assisted physical manipulation of the patient's 830 musculature or soft tissue via an electrotherapy glove described herein within the physical manipulation target region 835B of the neck region in an embodiment in which pain within the patient's 830 general area of complaint or treatment area (e.g., the gluteal muscles as described in FIG. 7B at 735) is referred pain or inefficiency caused by injury, inflammation, weakness, or overtaxed neck musculature. More specifically, physical manipulation target region 835B in an embodiment may include one or more cervical extensors along the back of the patient's 830 neck. As described in greater detail with respect to FIG. 10, below and with reference to FIG. 2, above, the amplitude-modulated pulsed direct current may also be transmitted to electrodes or fibers of the electrotherapy glove. The electrotherapy glove may have an outer patient contact surface of any portion that may be the treatment electrode in some embodiments. In other embodiments, electrodes in the electrotherapy glove may be situated at the practitioner's fingertips, or at the pad of the thumb (e.g., 222, 223, 224, 225, or 226 as shown in FIG. 2) for physical manipulation of the one or more cervical extensors along the back of the patient's 830 neck with the practitioner's fingers or thumb.

Figure 9:
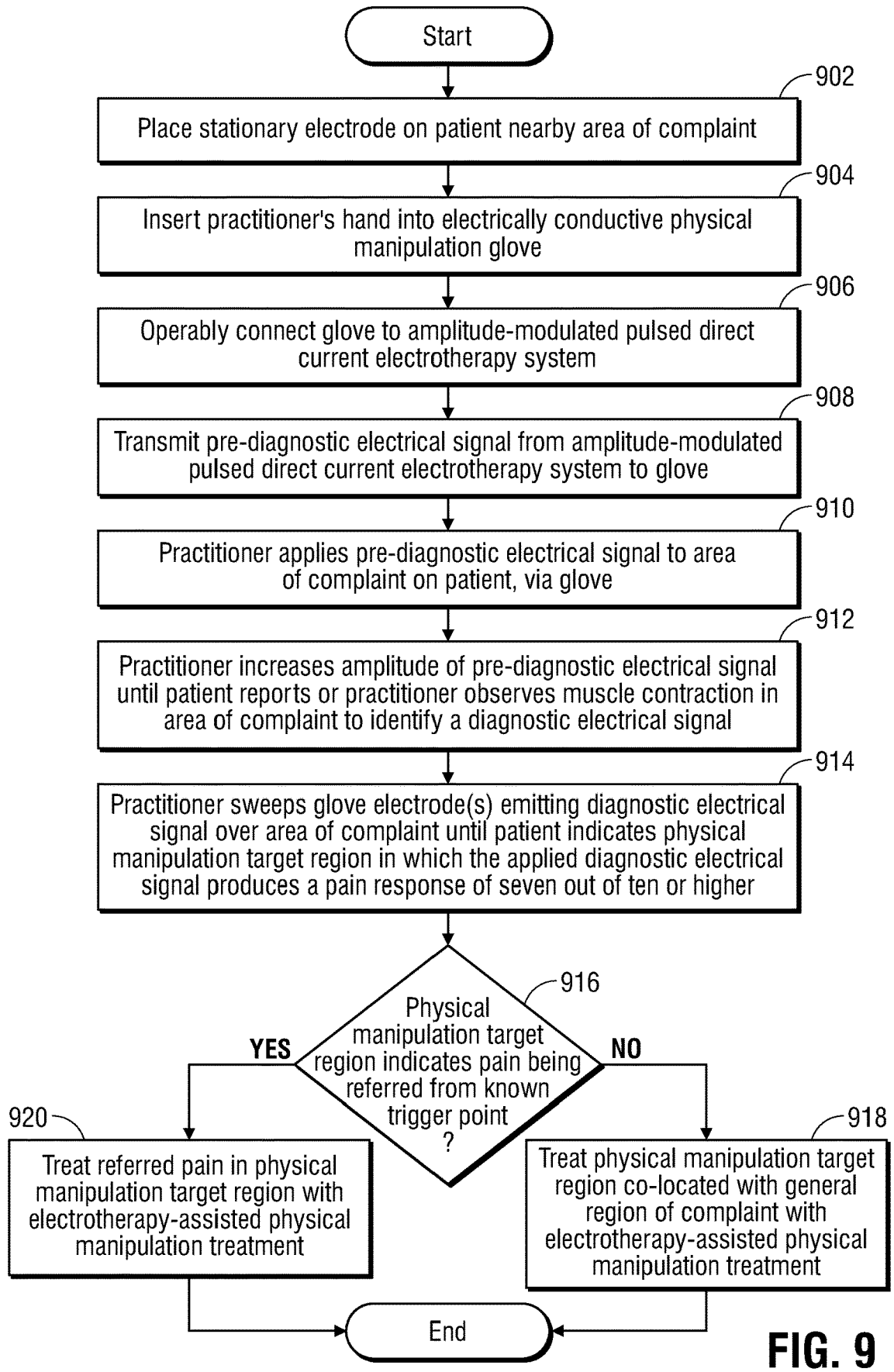
FIG. 9 is a flow diagram illustrating a method of locating a physical manipulation target region using an electrotherapy glove according to an embodiment of the present disclosure.

FIG. 9 is a flow diagram illustrating a method of locating a physical manipulation target region for electrotherapy-assisted physical manipulation of a patient's musculature using an electrotherapy glove according to an embodiment of the present disclosure. As described herein, the practitioner may use the electrotherapy glove in various embodiments to identify or diagnose the physical manipulation target region.

At block 902, a stationary electrode may be placed on the patient nearby an area of complaint or treatment area identified by the patient in an embodiment. For example, in an embodiment described with respect to FIG. 1, an amplitude-modulated pulsed direct current electrotherapy signal generator 110 in an embodiment may transmit an amplitude-modulated pulsed DC electrical signal to an electrode 113 situated within a physical manipulation target region 131 of a patient's musculature via an electrically conductive cable or wire 112. In other embodiments, the electrode may be placed anywhere on the patient's body, not necessarily within the physical manipulation target region 131 or the patient's general area of complaint or practitioner-estimated treatment area.

The practitioner's hand may be inserted within an electrotherapy glove having an electroconductive exterior surface in an embodiment at block 904. For example, as described in an embodiment with respect to FIG. 2, an amplitude-modulated pulsed DC electrical signal in an embodiment may be applied to a patient during physical manipulation of a patient's musculature or soft tissues (e.g., physical therapy or manual therapy) by a practitioner via an electrotherapy glove 220 worn by the practitioner 222, or during diagnosis or location of a physical manipulation target region on a patient. The entire exterior surface of the electrotherapy glove 220 in an embodiment may operate as a single electrode. In other embodiments, one or more electrodes (e.g., 222, 223, 224, 225, 226, 227, 228, or 229) may be placed along the exterior of the electrotherapy glove at positions relative to the practitioner's hand commonly used in various physical manipulation techniques. In yet another embodiment, the practitioner may select one or more among the plurality of electrodes (e.g., 222, 223, 224, 225, 226, 227, 228, or 229) to emit the amplitude-modulated pulsed DC electrical signal based on the physical manipulation technique employed at any given time.

At block 906, the electrotherapy glove in an embodiment may be operably connected to the amplitude-modulated pulsed direct current electrotherapy system in an embodiment. For example, in an embodiment described with respect to FIG. 1, the amplitude-modulated pulsed direct current electrotherapy signal generator 110 may also transmit the amplitude-modulated pulsed DC electrical signal to a receiving port 121 of an electrotherapy glove 120 worn by a practitioner 122, via an electrically conductive cable or wire 111.

A pre-diagnostic electrical signal may be transmitted from the amplitude-modulated pulsed direct current electrotherapy system to the electrotherapy glove worn by the practitioner, or to selected electrodes on the electrotherapy glove in an embodiment at block 908. For example, the practitioner 122 may use the electrotherapy glove 120 to identify or diagnose the physical manipulation target region 131 by beginning with a patient 130 identifying a general area of complaint or treatment area that is causing the patient 130 discomfort or pain. The practitioner 122 may apply the stationary electrode 113 within the general area of complaint or treatment area (or anywhere on the patient's body), and initially instruct the amplitude-modulated pulsed DC electrotherapy signal generator 110 to produce a pre-diagnostic electrical signal having an amplitude (e.g., at or below one Volt) relatively lower than that routinely used during therapeutic physical manipulation.

At block 910, the practitioner may apply the pre-diagnostic electrical signal to the area of complaint or treatment area on the patient, via the electrotherapy glove or via selected electrodes on the electrotherapy glove. For example, in an embodiment described with reference to FIG. 1, the practitioner 122 may apply the pre-diagnostic electrical signal to the patient's general area of complaint or treatment area via contact between the electrotherapy glove 120 and a portion of the patient's skin within the general area of complaint or treatment area, causing the patient's musculature or soft tissue to conduct the pre-diagnostic electric signal between the electrotherapy glove 120 and the electrode 113. As described in an embodiment with reference to FIG. 2, the electrotherapy glove 220 in an embodiment may deliver the amplitude-modulated pulsed DC electrical signal, the pre-diagnostic electrical signal, or the diagnostic electrical signal to a patient's skin through one or more electrodes (e.g., 222, 223, 224, 225, 226, 227, 228, or 229) situated at various locations along the exterior surface of the electrotherapy glove 220, or through electrically conductive fibers interwoven within the exterior surface of the electrotherapy glove 220, or through selected electrodes on the electrotherapy glove (e.g., 222, 223, 224, 225, 226, 227, 228, or 229) and operably connected to the port 221.

The practitioner may increase the amplitude of the pre-diagnostic electrical signal in an embodiment at block 912 until the patient reports or the practitioner observes muscle contraction within the area of complaint or treatment area to identify a diagnostic electrical signal of the increased amplitude. As described in an embodiment with respect to FIG. 3, for example, a knob or other input device 303 in an embodiment may be used in order to adjust an amplitude or a frequency of a pulsed DC electrical signal, including the pre-diagnostic electrical signal. As also described in an example embodiment with respect to FIG. 1, the practitioner 122 may use such a knob to slowly increase the amplitude (e.g., voltage) of the applied electrical signal until the patient reports, or the practitioner observes a contraction of the patient's musculature between or surrounding the electrotherapy glove 120 and the electrode 113. This observation may indicate an amplitude (e.g. voltage) the practitioner may use to instruct the amplitude-modulated pulsed DC electrotherapy signal generator 110 to generate a diagnostic electrical signal that the practitioner 122 may use to more specifically identify a physical manipulation target region 131 that may be treated to address the patient's discomfort or pain within the general area of complaint or treatment area.

The practitioner in an embodiment at block 914 may sweep the electrotherapy glove electrodes emitting the diagnostic electrical signal identified at block 912 over the area of complaint or treatment area until the patient identifies a physical manipulation target region in which the applied diagnostic electrical signal produces a pain response at a threshold level on a pain scale (e.g., seven out of ten or higher), as indicated by the patient. For example the practitioner 122 in an embodiment may identify a specific physical manipulation target region 131 in an embodiment by gauging the level of a patient's pain or discomfort during application of the diagnostic electrical signal (e.g., having an amplitude sufficient to produce muscle contraction) across various points within the patient's 130 general area of complaint or treatment area. For example, the practitioner 122 in an embodiment may sweep the electrotherapy glove 120 or one or more practitioner-selected electrodes within the electrotherapy glove 120 (e.g., as described in greater detail with respect to FIG. 2) across several locations on the patient's 130 upper torso if the patient is complaining of discomfort or pain within the chest area. In such an embodiment, the practitioner 122 may instruct the patient 130 to indicate when application of the diagnostic electrical signal via the electrode 113 and the electrotherapy glove 120 produce a sensation of pain having an intensity at or above a threshold level on a pain scale, such as seven on a pain scale from one to ten. A physical manipulation target region 131 in an embodiment may be identified by locating such an area or point where application of the diagnostic electrical signal at the amplitude capable of producing muscle contraction produces a pain or discomfort sensation in the patient 130 having an intensity at or above the pain scale threshold.

At block 916, the practitioner may determine whether the physical manipulation target region identified at block 914 indicates that the patient's pain is being referred from a known trigger point. As described herein, identification of the area in which the diagnostic electrical signal produces a pain response of roughly seven out of ten in the patient may indicate a physical manipulation target region co-located with the patient's general area of complaint or treatment area, or a region located separately or relatively distantly from the location of the pain response. The diagnostic electrical signal may be identifying a trigger point or referred pain associated with an injury in a different location. If the physical manipulation target region is not associated with a known trigger point, this may indicate that the patient's pain is being caused by musculature within the physical manipulation target region, and the method may proceed to block 918 for treatment of musculature within the physical manipulation target region. If the physical manipulation target region indicates that the patient's pain is being referred from a known trigger point, the method may proceed to block 920 for treatment of the trigger point area.

At block 918, in an embodiment in which the physical manipulation target region is not associated with a known trigger point, the practitioner may treat the physical manipulation target region with an electrotherapy-assisted physical manipulation treatment. For example, in an embodiment described with reference to FIGS. 7A and 8A in which the patient's general area of complaint or treatment area 731 is the forearm, the practitioner may treat the physical manipulation target region 831, as described in greater detail with respect to FIG. 10, below. The method for locating a physical manipulation target region in which a patient has identified a pain response may then end.

In an embodiment in which the physical manipulation target region is associated with a known trigger point outside of the physical manipulation target region, the practitioner at block 920 may treat the known trigger point with an electrotherapy-assisted physical manipulation treatment. For example, in an embodiment described with reference to FIGS. 7B and 8A in which the patient's general area of complaint or treatment area 734 is the upper back, the practitioner may treat the physical manipulation target region 834C including the pectoral muscles, clavicular muscles, or subclavicular soft tissues, as described in greater detail with respect to FIG. 10, below. The method for locating a trigger point causing referred pain within a physical manipulation target region may then end.

Figure 10:
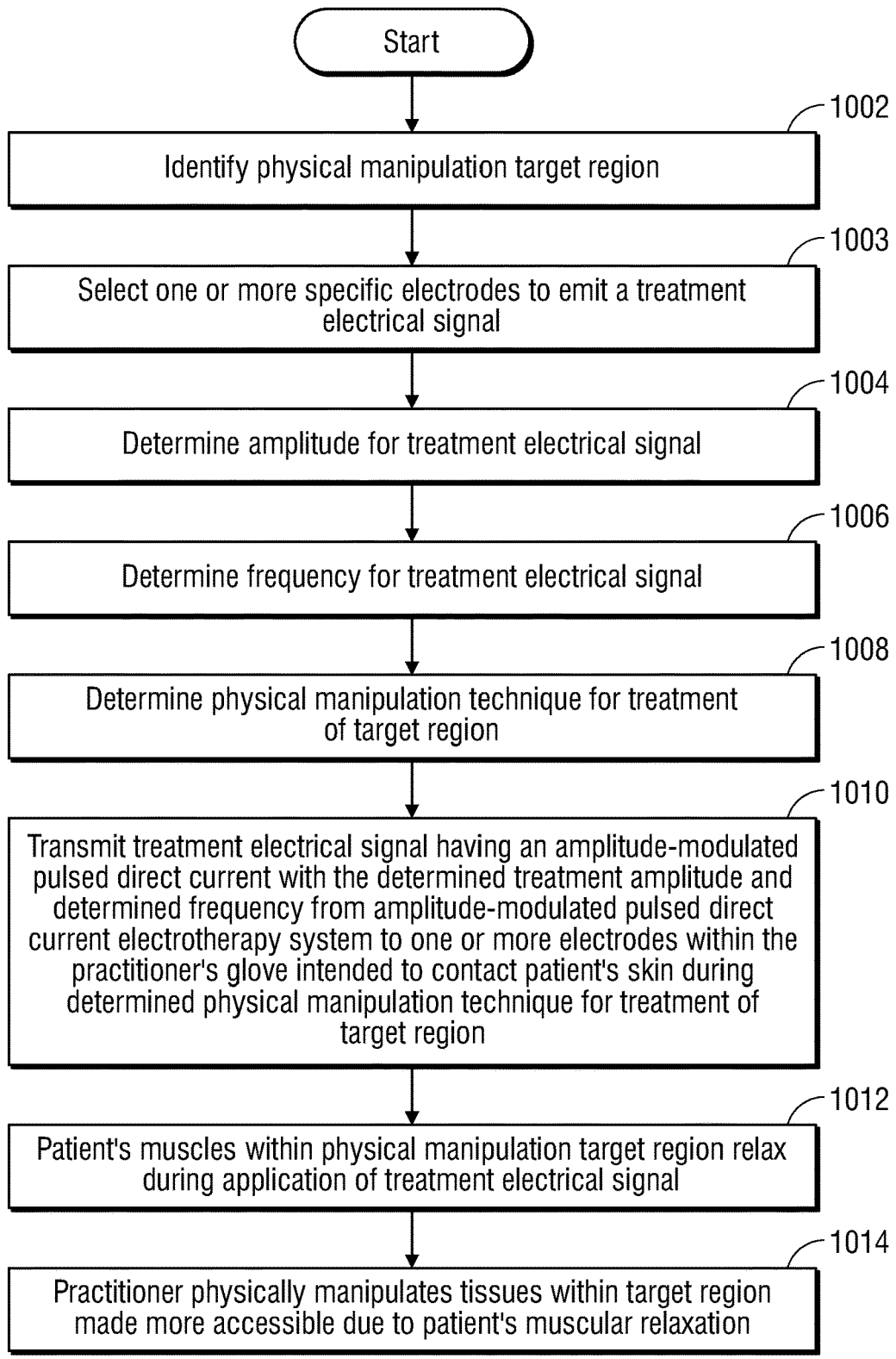
FIG. 10 is a flow diagram illustrating a method of treating a patient within a physical manipulation target region via an electrotherapy glove according to an embodiment of the present disclosure.

FIG. 10 is a flow diagram illustrating a method of treating a patient within a physical manipulation target region by applying electrotherapy-assisted physical manipulation via an electrotherapy glove according to an embodiment of the present disclosure. As described herein, upon identification of the physical manipulation target region in an embodiment (e.g., as described above with respect to FIG. 9), the practitioner may perform electrotherapy-assisted physical manipulation treatment of the patient's musculature or soft tissue within the physical manipulation target region.

At block 1002, a physical manipulation target region may be identified in an embodiment. For example, in an embodiment described with respect to FIG. 9 above at block 918, a physical manipulation target region co-located or overlapping the patient's general area of complaint or treatment area may be identified. As another example, in an embodiment described with respect to block 920, a physical manipulation target region located distantly from the patient's general area of complaint or treatment area and associated with a trigger point or referred pain may be identified.

At block 1003, a practitioner may optionally select one or more electrodes on the electrotherapy glove to emit a treatment electrical signal to be used during physical manipulation in an embodiment. For example, as described in an embodiment with respect to FIGS. 2 and 3, the practitioner in an embodiment may further direct the amplitude-modulated pulsed direct current electrotherapy signal generator 210 via the electrode switch selector 212 to transmit the amplitude-modulated pulsed DC electrical signal to a specific electrode (e.g., 222, 223, 224, 225, 226, 227, 228, or 229) or combination thereof on the electrotherapy glove 220, or to transmit the signal through all electrodes (e.g., 222, 223, 224, 225, 226, 227, 228, or 229) or through an interwoven electrically conductive fabric simultaneously in various embodiments. For example, the practitioner may use the electrode switch selector 212 with the amplitude-modulated pulsed DC electrotherapy signal generator 210 to select one or more of the electrotherapy glove electrodes (e.g., 222, 223, 224, 225, 226, 227, 228, or 229), or a combination thereof to emit the amplitude-modulated pulsed DC electrical signal. More specifically, the practitioner in an example embodiment may select (e.g., via one or more buttons or through manipulation of a user interface on the amplitude-modulated pulsed DC electrotherapy signal generator 210) to emit the amplitude-modulated pulsed DC electrical signal through the electrode 228 corresponding to the heel of the practitioner's palm. As another example embodiment, the practitioner may select to emit the amplitude-modulated pulsed DC electrical signal through the electrodes 223, 224, 225, and 226 corresponding to the practitioner's fingertips. In still another example embodiment, the practitioner may select to emit the amplitude-modulated pulsed DC electrical signal through the electrodes 222, 223, and 224 corresponding to the practitioner's thumb and tips of the practitioner's index and middle fingers. These are only a few examples of selections that may be made for specific electrodes within the electrotherapy glove 220, and all possible combinations of electrodes operably connected to the port 221 are also contemplated herein. It is contemplated in some embodiments that the entire exterior surface of the electrotherapy glove may operate as a single electrode.

A practitioner may determine an amplitude for a treatment electrical signal to be used during physical manipulation of the identified physical manipulation target region in an embodiment at block 1004. For example, in an embodiment described with respect to FIG. 1, the practitioner 122 may determine an amplitude and frequency of a therapeutic pulsed DC electrical signal underlying an amplitude-modulated pulsed DC treatment electrical signal to apply to the patient 130 within the physical manipulation target 131 region via the electrotherapy glove 120. As described with respect to FIG. 3, a knob or other input device 303 in an embodiment may be used in order to adjust an amplitude or a frequency of a pulsed DC electrical signal in an embodiment.

In an example embodiment described with reference to FIG. 6, the amplitude-modulated pulsed DC current electrotherapy system in an embodiment may generate an amplitude-modulated pulsed DC electrical signal comprising a pulsed DC electrical signal mixed with an AC signal to attain the benefits of each. Existing electrotherapy systems are known to apply either a DC electrical signal or an AC electrical signal. For example, DC signals pulsed at high frequencies (e.g., 100 to 1000 Hz) have been shown to decrease muscle contraction. However, such DC signals may cause a patient to experience a prickling, hot, or painful sensation at the site of application. In contrast, AC signals decrease or inhibit the prickling, hot, or painful sensations felt by patients during application of direct current, but have been shown to cause muscle contraction, rather than the muscle relaxation caused by application of DC signals.

The pulsed DC electrical signal that is combined with an AC signal to generate the amplitude-modulated pulsed DC treatment electrical signal in an embodiment may include pulses of peak amplitude 640 (e.g., between 4 and 5 Volts) occurring at regular intervals (e.g., 620, 621, 622, 623, respectively). The practitioner in an embodiment may determine an appropriate amplitude for a treatment electrical signal in an embodiment based on previous sessions with the same patient and for the same physical manipulation target region. In other embodiments, the practitioner may initially set the amplitude of the pulsed DC electrical signal underlying the amplitude-modulated pulsed DC therapeutic electrical signal to the lower end of a known range of therapeutic amplitudes (e.g., around 4 volts), and slowly increase the amplitude until the patient reports or the practitioner observes relaxation of the musculature within the physical manipulation target region.

At block 1006, a practitioner may determine a frequency for the treatment electrical signal. As described above at block 1004, the practitioner 122 may determine an amplitude and frequency of a therapeutic pulsed DC electrical signal underlying an amplitude-modulated pulsed DC treatment electrical signal to apply to the patient 130 within the physical manipulation target 131 region via the electrotherapy glove 120. At block 1006, the practitioner 122 in an embodiment may choose a frequency anywhere between one and 1,000 Hz for the therapeutic pulsed DC electrical signal. In a specific embodiment, the therapeutic DC electrical signal may produce pulses of voltage (e.g., between one and five Volts) at a frequency of around 500 Hz (e.g., between 425 and 575 pulses per second). The practitioner in an embodiment may determine an appropriate frequency for a treatment electrical signal in an embodiment based on previous sessions with the same patient and for the same physical manipulation target region. In other embodiments, the practitioner may initially set the frequency of the pulsed DC electrical signal underlying the amplitude-modulated pulsed DC therapeutic electrical signal to the lower end of a known range of therapeutic frequencies (e.g., below 400 Hz), and slowly increase the frequency until the patient reports or the practitioner observes relaxation of the musculature within the physical manipulation target region.

An electrical signal having an amplitude-modulated pulsed direct current with the determined treatment amplitude and treatment frequency may be transmitted from the amplitude-modulated pulsed direct current electrotherapy system to the entire exterior surface of the electrotherapy glove 120 or to one or more electrodes within the practitioner's electrotherapy glove 120 selected as in an optimal embodiment described above with reference to block 1003 in an embodiment at block 1008. For example, in an embodiment described with respect to FIG. 1, the electrotherapy glove 120 in an embodiment may deliver the amplitude-modulated pulsed DC therapeutic electrical signal through the one or more electrodes situated at various locations along the exterior surface of the electrotherapy glove 120, or through electrically conductive fibers interwoven within the exterior surface of the electrotherapy glove 120. More specifically, in an embodiment described with reference to FIG. 2, the electrotherapy glove 220 in an embodiment may deliver the amplitude-modulated pulsed DC electrical signal, the pre-diagnostic electrical signal, or the diagnostic electrical signal to a patient's skin through one or more electrodes (e.g., 222, 223, 224, 225, 226, 227, 228, or 229) situated at various locations along the exterior surface of the electrotherapy glove 220, or through electrically conductive fibers interwoven within the exterior surface of the electrotherapy glove 220 and operably connected to the port 221.

In an example embodiment described with reference to FIG. 8A, the physical manipulation target region 836 for an electrotherapeutic manipulation intended as a global preventative measure may include the diaphragm muscles, or muscles along the ribs. The diaphragmatic muscles, in particular, may tense or contract when the brain senses that the patient is at risk or in a potentially dangerous situation. This stress response may also result in less than optimal use of other muscles throughout the body, in order to preserve resources for response to the perceived threat. In order to work toward more optimal use of muscles, it may be helpful to signal the brain that the patient's body is no longer in a dangerous situation in need of such an over reaching stress response. Causing relaxation of the diaphragmatic muscles in an embodiment may provide such a signal to the brain, which may then allow the remaining muscles to more efficiently access resources previously reserved for response to the perceived threat.

In such an embodiment, the amplitude-modulated pulsed direct current with the determined treatment amplitude and treatment frequency may be switched to be transmitted to electrodes or fibers of the electrotherapy glove situated at the practitioner's fingertips, or at the pad of the thumb (e.g., 222, 223, 224, 225, or 226 as shown in FIG. 2) for physical manipulation of the patient's diaphragm or rib musculature with the practitioner's fingers or thumb. In another example embodiment described with reference to FIG. 8A, the physical manipulation target region 831 including the patient's forearm may include the brachioradialis, or pronator teres muscles. In such an embodiment, the amplitude-modulated pulsed direct current may also be switched to be transmitted to electrodes or fibers of the electrotherapy glove situated at the practitioner's fingertips, or at the pad of the thumb (e.g., 222, 223, 224, 225, or 226 as shown in FIG. 2) for physical manipulation of the patient's brachioradialis, or pronator teres musculature with the practitioner's fingers or thumb.

In yet another example embodiment described with reference to FIG. 8A, the physical manipulation target region 832A may include the patient's psoas muscle and nearby musculature. In such an embodiment, the amplitude-modulated pulsed direct current may also be switched to be transmitted to electrodes or fibers of the electrotherapy glove situated at the practitioner's fingertips, or at the pad of the thumb (e.g., 222, 223, 224, 225, or 226 as shown in FIG. 2) and to electrodes or fibers situated at the heel of the practitioner's palm (e.g., 228) for physical manipulation of the patient's psoas, obliques along the iliac crest, or origin of the iliacus musculature with the practitioner's fingers, thumb, or heel of palm. In another example embodiment, the physical manipulation target region 832B may include the patient's adductor muscles. In such an embodiment, the amplitude-modulated pulsed direct current may also be switched to be transmitted to electrodes or fibers of the electrotherapy glove situated at the practitioner's fingertips, or at the pad of the thumb (e.g., 222, 223, 224, 225, or 226 as shown in FIG. 2) and to electrodes or fibers situated at the heel of the practitioner's palm (e.g., 228) for physical manipulation of the patient's adductor muscles with the practitioner's fingers, thumb, or heel of palm.

In still another example embodiment described with reference to FIG. 8B, the physical manipulation target region 832D may include the anterior segment of the gluteus medius muscle or the tensor fascia latae muscle. In such an embodiment, the amplitude-modulated pulsed direct current may also be switched to be transmitted to electrodes or fibers of the electrotherapy glove situated at the practitioner's fingertips, or at the pad of the thumb (e.g., 222, 223, 224, 225, or 226 as shown in FIG. 2) or to electrodes or fibers situated at the heel of the practitioner's palm (e.g., 228) for physical manipulation of the patient's anterior segment of the gluteus medius muscle or the tensor fascia latae muscle with the practitioner's fingers, thumb, or heel of palm. In yet another example embodiment, the physical manipulation target region 832C may include one or more spinal extensors from the vertebrae from the fifth lumbar (L5) to the sixth thoracic (T6). In such an embodiment, the amplitude-modulated pulsed direct current may also be switched to be transmitted to electrodes or fibers of the electrotherapy glove situated at the practitioner's fingertips, or at the pad of the thumb (e.g., 222, 223, 224, 225, or 226 as shown in FIG. 2) or to electrodes or fibers situated at the heel or outside of the practitioner's palm (e.g., 228 or 229) for physical manipulation of the one or more spinal extensors from the vertebrae from the fifth lumbar (L5) to the sixth thoracic (T6) with the practitioner's fingers, thumb, or heel or outside of palm.

In still another example embodiment described with reference to FIG. 8A, the physical manipulation target regions 833A and 833B may include the fibularis longus muscle and the tibilias posterior muscle, respectively. In such an embodiment, the amplitude-modulated pulsed direct current may also be switched to be transmitted to electrodes or fibers of the electrotherapy glove situated at the practitioner's fingertips, or at the pad of the thumb (e.g., 222, 223, 224, 225, or 226 as shown in FIG. 2) for physical manipulation of the patient's fibularis longus muscle or the tibilias posterior muscle with the practitioner's fingers or thumb. In yet another embodiment, the physical manipulation target region 835A may include the muscles of the jawbone posterior to the temporomandibular joint (TMJ). In such an embodiment, the amplitude-modulated pulsed direct current may also be switched to be transmitted to electrodes or fibers of the electrotherapy glove situated at the practitioner's fingertips, or at the pad of the thumb (e.g., 222, 223, 224, 225, or 226 as shown in FIG. 2) for physical manipulation of the patient's muscles of the jaw bone posterior to the temporomandibular joint (TMJ) with the practitioner's fingers or thumb. In still another embodiment described with reference to FIG. 8B, the physical manipulation target region 835B may include one or more cervical extensors along the back of the patient's 830 neck. In such an embodiment, the amplitude-modulated pulsed direct current may also be switched to be transmitted to electrodes or fibers of the electrotherapy glove situated at the practitioner's fingertips, or at the pad of the thumb (e.g., 222, 223, 224, 225, or 226 as shown in FIG. 2) for physical manipulation of the one or more cervical extensors along the back of the patient's 830 neck with the practitioner's fingers or thumb.

In another example embodiment described with reference to FIG. 8A, the physical manipulation target region 834C may include the clavicular pectoral muscles or subclavius muscles and soft tissue. In such an embodiment, the amplitude-modulated pulsed direct current may also be switched to be transmitted to electrodes or fibers of the electrotherapy glove situated at the practitioner's fingertips, outside of the palm, or at the pad of the thumb (e.g., 222, 223, 224, 225, or 226 as shown in FIG. 2) or knuckles (e.g., 227 as shown in FIG. 2) on the top side of the electrotherapy glove for physical manipulation of the clavicular pectoral muscles or subclavius muscles and soft tissue with the practitioner's fingers, thumb or knuckles. In still another embodiment described with reference to FIG. 8B, for example, the physical manipulation target regions 834A and 834B may include one or more scalene muscles and spinal extensors from the vertebrae from the first to sixth thoracic (T1 to T6), respectively. In such an embodiment, the amplitude-modulated pulsed direct current may also be switched to be transmitted to electrodes or fibers of the electrotherapy glove situated at the practitioner's fingertips, at the pad of the thumb (e.g., 222, 223, 224, 225, or 226 as shown in FIG. 2) or at the knuckles (e.g., 227 as shown in FIG. 2) on the backside of the glove for physical manipulation of the one or more scalene muscles or spinal extensors from the vertebrae from the first to sixth thoracic (T1 to T6) with the practitioner's fingers, thumb, or knuckles.

The above are optimal examples for using an optimal embodiment to switch among electrode regions on an electrotherapy glove. Any selection of a single electrode or combination of electrodes is contemplated as needed by a practitioner. Further the entire exterior surface of the electrotherapy glove may operate as a single electrode in an embodiment.

At block 1010, a patient's muscles within the physical manipulation target region may relax during application of the treatment electrical signal via the electrotherapy glove during the physical manipulation treatment. For example, in an embodiment described with reference to FIG. 1, the amplitude-modulated pulsed DC therapeutic electrical signal so applied in an embodiment may cause the patient's muscles within the physical manipulation target region 131 to relax upon application, without causing any painful or stinging sensations within the patient's soft tissues or skin, due to the mixing of the therapeutic pulsed DC electrical signal which causes muscle relaxation, and the AC electrical signal which blocks the flow of ions causing painful or stinging sensations. Such electrotherapy-assisted physical manipulation using the amplitude-modulated pulsed DC electrical signal may decrease unconscious muscle contraction or tensing during physical manipulation treatment, allowing the practitioner 122 to access deeper into muscle tissue within the physical manipulation target region 131 for more in-depth physical manipulation of injured, overworked, or weakened muscles.

The practitioner in an embodiment may physically manipulate tissues within the physical manipulation target region made more accessible due to the patient's muscular relaxation at block 1014. For example, in an embodiment described with reference to FIG. 8A, upon relaxation of the musculature within the physical manipulation target region 831, the practitioner may use the electrotherapy glove to palpate with the thumb, finger tips, or knuckles into the brachioradialis muscle, starting at the proximal end and working along the length of the muscle toward the distal end. The practitioner in such an embodiment may stop for a period of time, for example ten to thirty seconds, to apply consistent pressure at any sensitive areas and repeat the same process on the pronator teres musculature.

As another example described with reference to FIG. 8A, upon relaxation of the musculature within the physical manipulation target region 832A, the practitioner may use the electrotherapy glove to press the heel of the palm into the patient's abdomen, at the level of the navel on the lateral border of the rectus abdominis and move the tissue medially and laterally to patient tolerance. The practitioner in such an embodiment may further palpate along a 45 degree angle from the navel to the Anterior Superior Iliac Spine (ASIS), stopping for a period of time, for example ten to thirty seconds, to apply consistent pressure at any sensitive areas.

In still another example embodiment described with reference to FIG. 8A, upon relaxation of the musculature within the physical manipulation target regions 833A or 833B, the practitioner may use the electrotherapy glove to press through the gastric to find a trigger point, or mobilize the musculature along the upper two-thirds of the fibula. In yet another example embodiment, upon relaxation of the musculature within the physical manipulation target region 834C, the practitioner may use the electrotherapy glove to dig with the tip of the thumb under the clavicle, starting inferior and pressing deep and superior to wedge underneath the clavicle. In yet another example embodiment, upon relaxation of the musculature within the physical manipulation target region 836, the practitioner may palpate with the tip of the thumb or fingers from the xiphoid process along the costal margin, stopping for a period of time, for example ten to thirty seconds, to apply consistent pressure at any sensitive areas.

In an example embodiment described with reference to FIG. 8B, upon relaxation of the musculature within the physical manipulation target region 834A, the practitioner may use the electrotherapy glove to palpate with the tips of fingers or thumb from the origin of the anterior scalene, along the length of the muscle towards the insertion, stopping for a period of time, for example ten to thirty seconds, to apply consistent pressure at any sensitive areas. This process may be repeated in an embodiment for the middle scalene and posterior scalene. In another example embodiment, upon relaxation of the musculature within the physical manipulation target region 834B, the practitioner may use the electrotherapy glove to dig with the tip of the thumb or knuckles under the spinal erector muscles, starting lateral to the erectors and digging underneath them in a medial direction toward the spine to wedge under the erectors. In yet another example embodiment, upon relaxation of the musculature within the physical manipulation target region 835B, the practitioner may use the electrotherapy glove to apply pressure with the tip of the thumb, fingers, or knuckles along the cervical extensor muscles at the back of the neck, from the occipital ridge down to the seventh cervical vertebra (C7).

Such in-depth manipulation may promote quicker healing and more effectively decrease acute or chronic pain associated with muscular or soft tissue injury. In such a way, the amplitude-modulated pulsed direct current electrotherapy system may allow a practitioner to manipulate a patient's tissue made more accessible due to muscle relaxation resulting from application of the electrotherapy via an electrotherapy glove worn by the practitioner during such physical manipulation. The method for treating a patient using an electrotherapy glove may then end.

The invention has broad applicability and can provide many benefits as described and shown in the examples above. The embodiments will vary greatly depending upon the specific application, and not every embodiment will provide all of the benefits and meet all of the objectives that are achievable by the invention.

Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip.

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions, and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An amplitude-modulated pulsed direct current (DC) electrotherapy system comprising:
   an electrotherapy glove for insertion of a practitioner's hand and an exterior surface including an electrically conductive patient-contact surface for contacting a patient's skin during an electrotherapy-assisted physical manipulation treatment of the patient's muscle within a physical manipulation target region of a patient's body;
   an amplitude-modulated pulsed DC signal generator operably connected to the electrotherapy glove via an electrically conductive interface to deliver an amplitude-modulated pulsed DC electrical signal having a varying DC voltage corresponding to a pulsed DC electrical signal amplitude to the physical manipulation target region via the patient-contact surface of the electrotherapy glove; and
   the amplitude-modulated pulsed DC electrical signal incorporating an alternating current (AC) electrical signal to limit pain sensation in the patient's skin relative to application of a DC-only electrical signal within the physical manipulation target region and having a pulsed DC electrical signal frequency inducing relaxation of the patient's muscle due to application of the amplitude-modulated pulsed DC electrical signal to increase a portion of the patient's muscle and other tissue accessible to the practitioner for physical manipulation during the electrotherapy-assisted physical manipulation treatment.

2. The amplitude-modulated pulsed DC electrotherapy system of claim 1, wherein the pulsed DC electrical signal frequency is mixed with the AC electrical signal having an AC electrical signal amplitude that is lower than the pulsed DC electrical signal amplitude and an AC electrical signal frequency that is higher than the pulsed DC electrical signal frequency.

3. The amplitude-modulated pulsed DC electrotherapy system of claim 1, wherein the pulsed DC electrical signal amplitude is greater than one Volt.

4. The amplitude-modulated pulsed DC electrotherapy system of claim 1, wherein the pulsed DC electrical signal frequency is less than 1000 Hz.

5. The amplitude-modulated pulsed DC electrotherapy system of claim 1, wherein the exterior surface of the electrotherapy glove is comprised of electrically conductive fibers woven together such that the entirety of the exterior surface of the electrotherapy glove is electrically conductive.

6. The amplitude-modulated pulsed DC electrotherapy system of claim 1 further comprising:
   a switch selector to select an electrode of the electrically conductive patient-contact surface of the electrotherapy glove situated at a fingertip with respect to the practitioner's inserted hand for delivery of the amplitude-modulated pulsed DC electrical signal.

7. The amplitude-modulated pulsed DC electrotherapy system of claim 1 further comprising:
   a switch selector to select an electrode of the electrically conductive patient-contact surface of the electrotherapy glove situated at the heel of the palm with respect to the practitioner's inserted hand for delivery of the amplitude-modulated pulsed DC electrical signal.

8. A method of electrotherapy-assisted physical manipulation treatment comprising:
   applying a diagnostic electrical signal having a diagnostic signal frequency and a diagnostic signal amplitude to an area of complaint on a patient, via an electrically conductive electrotherapy glove worn by a practitioner having an exterior surface including an electrically conductive patient-contact surface for contacting a physical manipulation target region of the patient;
   determining the physical manipulation target region for the patient, based on patient feedback indicating a level of the patient's muscular pain or discomfort sensation pursuant to application of the diagnostic electrical signal;
   determining a pulsed direct current (DC) electrical signal frequency and a pulsed DC electrical signal amplitude for a pulsed DC electrical signal for inducing relaxation of a patient's muscle within the physical manipulation target region to increase a portion of the patient's muscle and other tissue accessible to the practitioner during execution of a physical manipulation technique;
   mixing an alternating current (AC) electrical signal for inhibiting painful sensation in a patient's skin with the pulsed DC electrical signal to form an amplitude-modulated pulsed DC electrical signal;

conducting the amplitude-modulated pulsed DC electrical signal to the patient's skin within the physical manipulation target region via an amplitude-modulated pulsed DC electrical signal generator and the electrically conductive patient-contact surface of the electrotherapy glove; and executing the physical manipulation technique.

9. The method of claim 8 further comprising:

selecting an electrode of the electrically conductive patient-contact surface of the electrotherapy glove situated at a tip of a thumb with respect to the practitioner's inserted hand for delivery of the amplitude-modulated pulsed DC electrical signal, via an electrode switch selector of the amplitude-modulated pulsed DC electrical signal generator.

10. The method of claim 8 further comprising:

selecting an electrode of the electrically conductive patient-contact surface of the electrotherapy glove situated at a joining of a palm and a plurality of fingers with respect to the practitioner's inserted hand for delivery of the amplitude-modulated pulsed DC electrical signal, via a switch selector of the amplitude-modulated pulsed DC electrical signal generator.

11. The method of claim 8 further comprising:

selecting an electrode of the electrically conductive patient-contact surface of the electrotherapy glove situated at an outside of a palm with respect to the practitioner's inserted hand for delivery of the amplitude-modulated pulsed DC electrical signal, via a switch selector of the amplitude-modulated pulsed DC electrical signal generator.

12. The method of claim 8 further comprising:

selecting a combination of electrodes of the electrically conductive patient-contact surface of the electrotherapy glove, each of the combination of electrodes situated at a plurality of fingertips with respect to the practitioner's inserted hand, for delivery of the amplitude-modulated pulsed DC electrical signal, via a switch selector of the amplitude-modulated pulsed DC electrical signal generator.

13. The method of claim 8 further comprising:

selecting a combination of electrodes of the electrically conductive patient-contact surface of the electrotherapy glove for delivery of the amplitude-modulated pulsed DC electrical signal, via a switch selector of the amplitude-modulated pulsed DC electrical signal generator;

wherein one of the combination of electrodes is situated at a fingertip with respect to the practitioner's inserted hand and one of the combination of electrodes is situated at a thumb of the practitioner's inserted hand.

14. The method of claim 8 further comprising:

determining the physical manipulation technique from a plurality of physical manipulation techniques, based on patient feedback indicating the level of the patient's muscular pain or discomfort sensation within the area of complaint pursuant to application of the diagnostic electrical signal.

15. An amplitude-modulated pulsed direct current (DC) electrotherapy system comprising:

an electrotherapy glove for insertion of a practitioner's hand and an exterior surface including an electrically conductive patient-contact surface for contacting a patient's skin during an electrotherapy-assisted physical manipulation treatment of the patient's muscle within a physical manipulation target region of a patient's body;

an amplitude-modulated pulsed DC signal generator operably connected to the electrotherapy glove via an electrically conductive interface to deliver an amplitude-modulated pulsed DC electrical signal formed by mixing a pulsed DC electrical signal and an alternating current (AC) electrical signal to the physical manipulation target region via the patient-contact surface of the electrotherapy glove;

the pulsed DC electrical signal having a varying DC voltage corresponding to a pulsed DC electrical signal amplitude and a pulsed DC electrical signal frequency inducing relaxation of the patient's muscle to increase a portion of the patient's muscle and other tissue accessible to the practitioner for physical manipulation during the electrotherapy-assisted physical manipulation treatment; and the amplitude-modulated pulsed DC electrical signal and having an AC electrical signal amplitude that is lower than the pulsed DC electrical signal amplitude and an AC electrical signal frequency that is higher than the pulsed DC electrical signal frequency applied to the physical manipulation target region.

16. The amplitude-modulated pulsed DC electrotherapy system of claim 15, wherein the AC electrical signal amplitude is equal to or less than one Volt.

17. The amplitude-modulated pulsed DC electrotherapy system of claim 1, wherein the pulsed DC electrical signal frequency is equal to or greater than ten Hz.

18. The amplitude-modulated pulsed DC electrotherapy system of claim 15, wherein the physical manipulation target region includes a muscle of the patient and the electrically conductive patient-contact surface of the electrotherapy glove incorporates an electrode situated at the fingertips pad with respect to the practitioner's inserted hand.

19. The amplitude-modulated pulsed DC electrotherapy system of claim 15, wherein the physical manipulation target region includes a muscle of the patient, and the electrically conductive patient-contact surface of the electrotherapy glove incorporates an electrode situated at the thumb pad with respect to the practitioner's inserted hand.

20. The amplitude-modulated pulsed DC electrotherapy system of claim 15, wherein the physical manipulation target region includes a muscle of the patient, and the electrically conductive patient-contact surface of the electrotherapy glove incorporates an electrode situated at the fingertips, thumb pad or knuckles with respect to the practitioner's inserted hand.

* * * * *